United States Patent
Olsen, II

(10) Patent No.: US 10,561,918 B2
(45) Date of Patent: Feb. 18, 2020

(54) METHOD AND APPARATUS FOR PROVIDING TRAINING TO A SURFER

(71) Applicant: Gilbert T Olsen, II, Point Pleasant, NJ (US)

(72) Inventor: Gilbert T Olsen, II, Point Pleasant, NJ (US)

( * ) Notice: Subject to any disclaimer, the term of this patent is extended or adjusted under 35 U.S.C. 154(b) by 515 days.

(21) Appl. No.: 15/217,962

(22) Filed: Jul. 22, 2016

(65) Prior Publication Data

US 2017/0021257 A1    Jan. 26, 2017

Related U.S. Application Data

(60) Provisional application No. 62/195,792, filed on Jul. 22, 2015.

(51) Int. Cl.
*A63B 69/00* (2006.01)
*A63B 71/06* (2006.01)
(Continued)

(52) U.S. Cl.
CPC ...... *A63B 69/0093* (2013.01); *A63B 71/0622* (2013.01); *E04H 4/0006* (2013.01); *G01S 17/88* (2013.01); *G06F 3/011* (2013.01); *G06F 9/453* (2018.02); *G09B 19/0038* (2013.01); *G09B 19/0076* (2013.01); *G09B 19/04* (2013.01); *G09B 19/06* (2013.01); *G16H 20/30* (2018.01); *A63B 2208/03* (2013.01); *A63B 2220/12* (2013.01); *A63B 2220/40* (2013.01); *A63B 2225/50* (2013.01)

(58) Field of Classification Search
CPC .............. A63B 69/0093; A63B 69/125; A63B 2022/0033; A63B 69/00; A63F 13/807; G06F 17/5009; G09B 19/0038; G09B 9/066

See application file for complete search history.

(56) References Cited

U.S. PATENT DOCUMENTS 4,522,535 A * 6/1985 Bastenhof ............. E04H 4/0006
  4/491
4,792,260 A * 12/1988 Sauerbier ........... A63B 69/0093
  4/491

(Continued)

*Primary Examiner* — Jerry-Daryl Fletcher
(74) *Attorney, Agent, or Firm* — Lawrence C. Edelman, Esq.

(57) ABSTRACT

Embodiments of the present invention provide a method and apparatus for providing training to a surfer. The method involves highlighting the critical elements of the surfing region, enabling a surfer to comprehend complex dynamic environments, (such as barrells), better understand what expert surfers do in such environments, and then progressing such maneuvers from the mind to the physical environment as actual performance. The apparatus comprises a sensory cue generator capable of delivering cues that enable a surfer to visualize maneuvers in their mind, practice in virtual/augmented reality, and the physical environment in artificially and naturally generated surfing conditions. The sensory cues are delivered dynamically to the surfer, in an intuitive fashion correlated with the surfing visualizations, simulations or environments, prompting the surfer to deploy correct surfing maneuvers, greatly reducing the learning curve and progressing physical and mental performance as never before.

6 Claims, 13 Drawing Sheets

(51) Int. Cl.
*G09B 19/00* (2006.01)
*E04H 4/00* (2006.01)
*G06F 9/451* (2018.01)
*G09B 19/04* (2006.01)
*G01S 17/88* (2006.01)
*G09B 19/06* (2006.01)
*G06F 3/01* (2006.01)
*G16H 20/30* (2018.01)

(56) References Cited

U.S. PATENT DOCUMENTS

| | | | | |
|---|---|---|---|---|
| 4,954,014 A | * | 9/1990 | Sauerbier | A63B 69/0093 4/491 |
| 2011/0212691 A1 | * | 9/2011 | Rott | H04B 1/3827 455/41.3 |
| 2011/0256518 A1 | * | 10/2011 | Rott | A63B 69/0093 434/247 |
| 2012/0201605 A1 | * | 8/2012 | Hill | A63B 69/0093 405/79 |
| 2013/0308064 A1 | * | 11/2013 | LaDuke | G03B 21/608 348/744 |
| 2017/0032693 A1 | * | 2/2017 | Regan | A63B 69/0093 |

\* cited by examiner

METHOD AND APPARATUS FOR PROVIDING TRAINING TO A SURFER

CROSS-REFERENCE TO RELATED APPLICATIONS

This application claims priority to U.S. provisional application No. 62/195,792 filed on Jul. 22, 2015, herein incorporated by reference in its entirety.

FIELD OF THE INVENTION

Embodiments of the present invention generally relate to the field of surfing, and more particularly to a method and apparatus for providing training to a surfer.

BACKGROUND

Surfing is a very popular water sport around the world. However, surfing is a difficult and complex skill to acquire because the surfing situations are very dynamic. Surfable waves, or surf waves are an outcome of a complex phenomenon between waves and underwater currents in the oceans, shallowing land towards the shore and the wind conditions. Since the constituent factors vary and change dynamically, the surfing conditions change dynamically as well, making it even more difficult for learners to reproduce situations in which they can repetitively practice a given skill set.

In addition to general difficulties in acquiring the skill of surfing, even more difficult is to acquire advanced surfing skills, such as 'pumping' on a face of a surf wave, 'stalling', 'cutbacks', 'off-the lips', 'floaters', 'aerials' or 'barrel' riding, and learners can sometimes spend months or years in learning or perfecting these skills.

With the advent of artificially generated surf waves, for example those using wave generation mechanisms in a pool, some of the dynamic conditions associated with surf waves are reduced, which may aid learners in training to surf. However, despite such artificially generated surf waves, advanced surfing skills remain difficult to learn, and even more difficult to perfect.

Therefore, there exists a need in the art for a method and apparatus for providing training to a surfer while surfing.

SUMMARY

Embodiments of the present invention provide a method and apparatus for providing training to a surfer while surfing, substantially as shown in and/or described in connection with at least one of the figures, as set forth more completely in the claims.

These and other features and advantages of the present disclosure may be appreciated from a review of the following detailed description of the present disclosure, along with the accompanying figures in which like reference numerals refer to like parts throughout.

DESCRIPTION

Figure 1A:
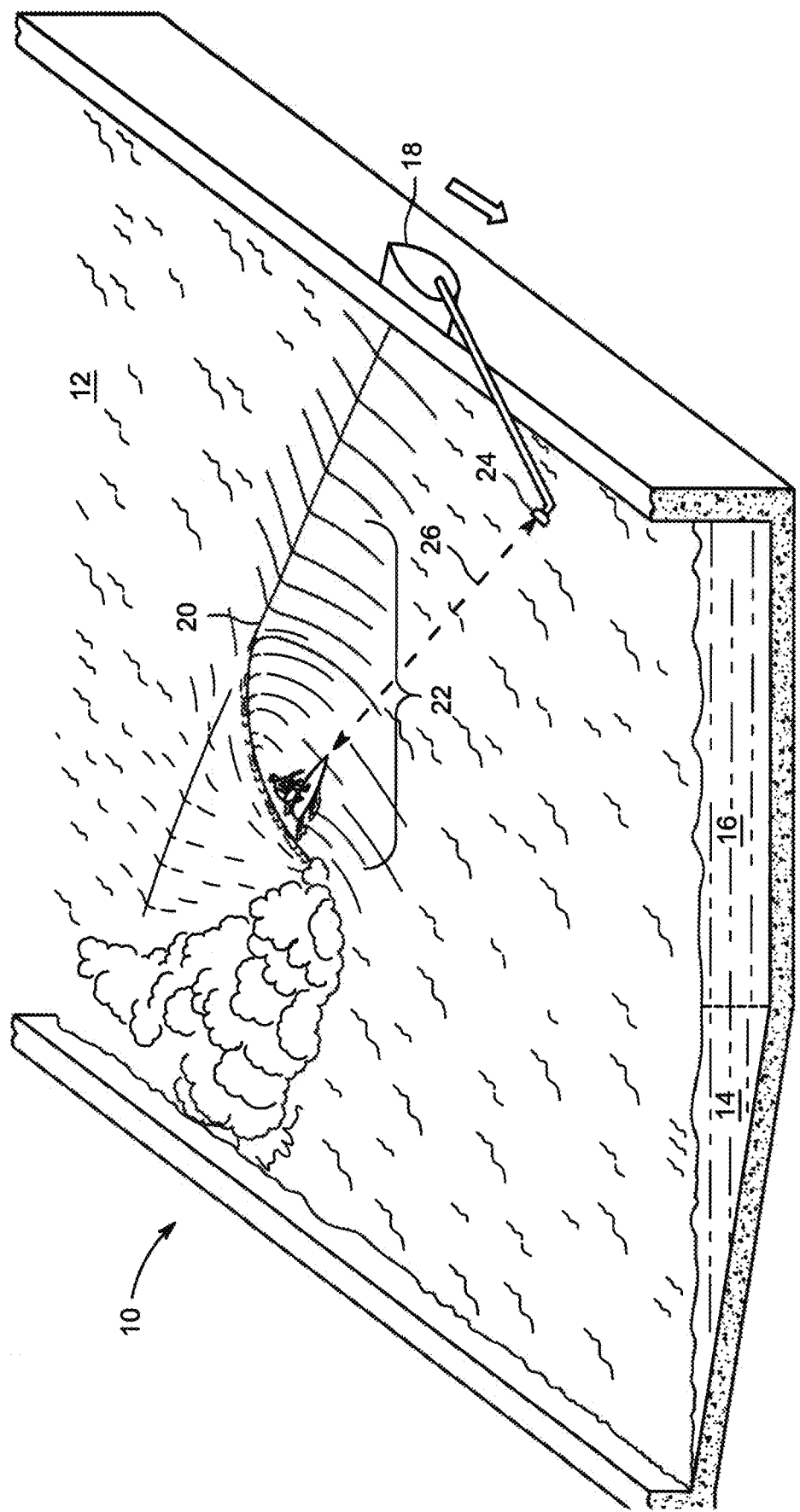
FIG. 1A depicts an apparatus for providing training to a surfer, for example, by providing sensory cues to the surfer while surfing in a pool having a linear motion wave generation mechanism, according to one or more embodiments.

Embodiments of the present invention provide a method and an apparatus for training a surfer, for example, while surfing a surf wave, by generating and delivering sensory cues to the surfer. The sensory cue(s) guide the surfer to implement a surfing maneuver, for example, manipulate his or her body, or mental state or approach and/or the surfboard to better surf the surf wave. The generation and delivery of sensory cues accounts for the dynamic motion of the surfer while surfing, and/or the dynamic nature of the surfing environment, including the motion of the surf wave, and/or the surfboard. Sensory cues are generated based on one or more of the position of the surf wave, position of a wave generation mechanism, position of the surfer, position of a surfboard being used by the surfer for surfing the surf wave, a predefined recommended path for surfing the surf wave, or a repository of surfing maneuvers. Sensory cues such as light, sound, touch (e.g. vibration), patterns thereof, on screen display including virtual or augmented reality displays are used to indicate surfing maneuvers to the surfer, while the surfer is surfing. Surfing maneuvers include indicating a recommended path, a discouraged path, manipulation of the body or the surfboard for affecting a particular motion, maneuvers for 'pumping' on a face of a surf wave, 'stalling', 'cutbacks', 'off-the lips', 'floaters', 'aerials', or 'barrel' riding among several other surfing maneuvers. Surfing related maneuvers include motions of the body and equipment in the surfing area that result in a surfer positioning for a wave, catching a wave, and riding it, ideally performing more advanced maneuvers such as trimming, pumping, bottom turns, top turns, cutbacks, off-the-lips, re-entries, floaters, aerials, and of course barrell riding. A desirable ride includes a variety of difficult maneuvers that demonstrate speed, power and flow in the most critical sections of the wave with a high degree of commitment, and may include a combination of one or more of the maneuvers discussed herein, and all such maneuvers are broadly referred to as "surfing maneuvers" or simply, "maneuvers".

In artificial surf wave generation pools, wave generation mechanisms including a foil to displace water in the pool, to generate a surf wave. The pool usually has a graded base with generally decreasing depth away from the foil. As the artificial wave generated by displacement of water by the foil travels away from the foil (foil swell region) into shallower region of the pool, the wave swells (shoulder and escape face sections) and further rises, and the rising water forms a lip, which plunges forward and curls (open barrel section) to generate a barrel as the curled water falls over (open where the curled water has not reached the water surface of the pool, closed barrel section where the curled water has impacted the water surface of the pool), simulating or replicating surfable waves approaching the shore in the oceans. In a portion of closed barrel section, there is whitewater turbulence inside the barrel due to the curled water falling on to the pool water surface. However, at least a portion of this closed barrel with whitewater turbulence is surfable or rideable, and this section is referred to as the foamball section. Further to the foamball section, the barrel ceases to exist and the surf wave is fully broken into whitewater, and this section is referred to as the fully broken section. Following the fully broken section, the surf wave diminishes further to merge with the ambient surface water of the pool, also referred to as the diminished and diminishing sections. The artificially generated surf wave including various patterns of swell, barrel and diminishing section travels synchronously and/or proportionally with the motion of the wave generating foil. The speed of the surf wave, the height of the swell and the barrels are a function of the profile of the pool, the profile of the base of the pool (also referred to as bathymetry), the profile of the foil, the velocity of the foil, among other factors generally known in the art of artificial wave generation. Typically, the surfable portion of the wave, including the swell region and the barrel region, travels generally parallel to the motion of the foil. Accordingly, a surfer surfing the moving artificially generated surf wave is generally within a defined surfable region in the pool, runs generally parallel to the motion of the wave generating foil. In pools having other than linear (rectangular orientations), such as circular or curvilinear pools, the motion of the wave generating foil corresponds to the circular or curvilinear profile of the pool, and the artificially generated surf wave moves in parallel with such motion of the wave generating foil. The orientation of the surfer is generally facing towards the side on which the wave generating foil is installed.

Accordingly, sensory cues are positioned for delivery to the surfer according to this defined surfable region in which the surfer is expected to be while surfing, and the relevant sensory mechanism of the surfer is exposed to the generated sensory cues, in order for the sensory cues to be sensed by the surfer while surfing. For example, several lamps may be installed along the defined surfable region in sequential strip, to face the surfer while the surfer is surfing in the defined surfable region. In examples where the surfer's orientation is to face towards the foil while surfing, the lamps are installed above the water, on the side along which the foil moves. In one example, the lamps directly in front of the surfer are illuminated, while the other lamps are switched off, and this sequence is repeated as the surfer moves forward along the surf wave. To the surfer, such illumination of lamps appears to travel alongside the surfer. The illuminated lamps generate light patterns that provide visual cues to the surfer to implement surfing maneuvers. Light from the lamps reflected on the surf wave also provides a visual cue to the surfer to implement a surfing maneuver. The lamps may also be installed under water at different locations with respect to the defined surfable region, or the sections of the surf wave, to generate light patterns on or within the surf wave to provide a visual cue to the surfer.

Sensory cue generators include lamps, multi-LED displays, liquid crystal displays, digital displays, audio speakers and the like, which may be installed in a similar fashion above the water and along the defined surfing region, to provide visual and auditory cues, respectively, to the surfer while surfing. For example, visual cues include illuminating lamps of different light colors, light patterns including laser projected patterns such as laser projection patterns, blinking patterns, reflections thereof, among others. As another example, multi-LED digital displays, such as those used for commercial signage may similarly be installed to deliver visual cues, such as single or multicolored icons, or even textual clues such as a text message. Similar and higher definition visual cues may also be provided by digital displays, similar to those used in LED televisions. Audio speakers installed similarly along the defined surfable region above water, to be audible to the surfer while surfing the surf wave provide auditory cues to the surfer while surfing. The auditory cues include sound of varying frequency, pitch, volumes, including specific instructions in a predefined language. In such examples, 'line of sight' of the surfer to the sensory cue is effective in delivering such sensory cues to the position of the surfer, and accordingly, the sensory cue generators are installed to be within a line of sight of the surfer.

In other examples, the sensory cues are delivered to the surfer without requiring a line of sight to the surfer. For example, auditory cues are transmitted wirelessly to a wireless headphone worn by the surfer, to deliver auditory cues similar to those described above. As another example, the digital displays are a virtual reality display or an augmented reality display worn by the user, to which data is transmitted wirelessly to provide visual and/or auditory cues to the surfer while surfing. The visual and/or auditory cues are superimposed or overlaid or presented along with a current viewpoint of the surfer. The superimposed visual and/or auditory cues may be turned on and off intermittently to provide assistance to the surfer during parts of surfing, and have the surfer surf without assistance during parts of surfing. In some embodiments, visual and/or auditory cues are superimposed or presented along with a video recording of a surfing session of the surfer, for example, for review of the surfing session of the surfer. In another example, vibratory cues are delivered to the user wirelessly to a vibration pad worn by the surfer. In this example, different vibration patterns and intensities are used to indicate a surfing maneuver to the surfer. One or more such auditory, visual, or touch-based sensory cues may be combined to enhance or supplement the sensory cues available to the surfer while surfing, to indicate surfing maneuvers to the surfer dynamically, and in real time as the surfer surfs the artificially generated surf wave. Sensory cues related to taste or smell may similarly be delivered to the surfer via corresponding delivery mechanisms, such as masks, nasal or oral regulators, that include delivery mechanisms to release, upon receiving a wireless signal, taste or smell agents to generate a sense of taste or smell for the surfer. All devices that generate sensory cues herein are generally referred to as sensory cue generators. In some embodiments, the sensor cues are generated by the sensory cue generators as a simulation, to be superimposed over a video of a surfing session, for example, captured from a viewpoint of a surfer surfing a surf wave. Various sensory cues as described herein may be superimposed, singly or in combination with other sensory cues, to present a simulated surfing session to the surfer, for enhanced training, for example, off the surfing arena, in a training room on dry-land, or in surfing simulation facility. Such simulation allows a surfer to visualize and rehearse maneuvers and different situations in their mind prior to or after experiencing them in an actual surfing environment.

The surfing maneuvers indicated by the surfing cues are based on one or more of the position of the surf wave (including the defined surfable region), the wave generating foil, position of the surfer (or the surfboard) on the surf wave, predefined surfing patterns, for example, surfing path or surfing maneuvers defined by surfing experts, or maneuvers defined according to the surfer's specific learning need or learning stage. These surfing maneuvers are suggested as sensory cues to the surfer in real time as the surfer is surfing in the defined surfing region or practicing on land/visualizing, and therefore, make it simpler for the surfer to implement a recommend surfing maneuver according the surfer's situation. In many case, while learning surfing, surfers are frustrated because while they implement the correct maneuvers, the maneuvers are not in the correct sequence, which leads inefficient surfing or complete failure in implementing a complex maneuver. For example, for a beginning surfer, it is a challenge to begin riding a wave, for which, mounting the surfboard properly is a first challenge that many surfers take a long time to perfect. According to embodiments of the invention, sensory cues are generated in a sequence to recommend maneuvers to the surfer in an effective or correct biomechanical progression of implementing such surfing maneuvers. For the example of mounting the surfboard, the sensory cues are generated in an order to indicate the surfer to first position the feet wide, then bend the knees, then straighten the back and then align the head forward. Such a real-time guidance reduces the learning curve and the frustration in mastering a new complex maneuver relatively simpler for the surfer. Further, having a recommended maneuver allows a learning surfer to focus on implementing the recommended maneuver, instead of having to interpret the dynamic and complex pattern of the surf wave, and select from the various complex surfing maneuvers, a process that requires several iterations to develop competency. In general, learning surfing by the process of trial and error can take several month or even years for most surfers. Availability of such recommended surfing maneuvers greatly reduces the learning curve of a surfer in practicing, honing and mastering complex surfing maneuvers, thereby offering unparalleled training and competency resource.

FIG. 1A illustrates an artificial wave generation pool 10 in a rectangular configuration, according to various embodiments. The artificial wave generation pool 10 comprises a rectangular pool 12 of water and an artificial wave generation mechanism (not shown) that generates an artificial wave, which travels along the length of the pool 12. The pool 12 has a deep region 16 adjacent to a foil 18, which is a part of the artificial wave generation mechanism, and a shallow region 14 adjoining the deep region 16. The shallow region 14 has base profile with depth that reduces in a direction moving away from the deep region 16. The foil 18 is either partially, or fully submerged in water, and as the foil 18 is moved along a side of the pool 12, water displaced by the foil generates a wave 20, which moves towards the shallow region 14. Without being bound by underlying theory or accuracy thereof, it is observed that as the wave travels from the deep region 16 to the shallow region 14, the motion of the wave causes the water to swell, rise, develop a lip which plunges forward to fall on the surface of the water generating a 'barrel', and proceed to dissipate into foamed water, replicating surfable waves generated in oceans near a shore. The regions in which the water swells, rises and part of the region in which the water plunges forward to fall creating a barrel or a tube, are suitable for surfing, and are defined as a surfable region 22. Since the generated wave 20 moves in the same direction as the foil 18, the patterns (such as the surfable region) within the generated wave 20 move along with the generated wave 20 along the length of the pool 12. The foil 18 leads the generated wave 20 and the sections therein, and each section of the generated wave 20 trails the foil 18 within a particular time range, such that the generated wave 20 and portions thereof are synchronized with the movement of the foil 18.

According to some embodiments, a sensory cue generator 24 is mechanically coupled to the foil 18, and moves along with the foil 18 while generating sensory cues. The sensory cue generator 24 is positioned relative to the surfable region 22 such that the sensory cue generator 24 is in a line of sight 26 from the surfable region 22 of the generated wave 20. As the foil 18 moves, generating the wave 20, which moves synchronously with the foil 18, the sensory cue generator 24 also moves synchronously to the generated wave 20. Due to this synchronization, the sensory cue generator 24 continues to be within the line of sight 26 from the surfable region 22 of the generated wave 20, as the generated wave 20 moves along the pool 12. The synchronized movement of the sensory cue generator 24 and the generated wave 20 enables a surfer surfing the surfable portion of the generated wave 20 in perceiving the sensory cue generated by the sensory cue generator 24 throughout the motion of the generated wave 20 across the pool 12. Such an arrangement of the sensory cue generator 24 is suitable for visual cue generators such as lamps, digital displays, or auditory cue generators such as audio speakers. While it is efficient to position audio speakers within a line of sight of the surfer, it is not necessary, because increasing the volume of the audio speaker may enable a surfer in hearing an auditory cue without a line of sight to the audio speakers. In some embodiments, the lamps or digital displays are positioned under water to generate patterns that are visible in the surfable region through the water, and therefore, in an indirect line of sight.

Figure 1B:
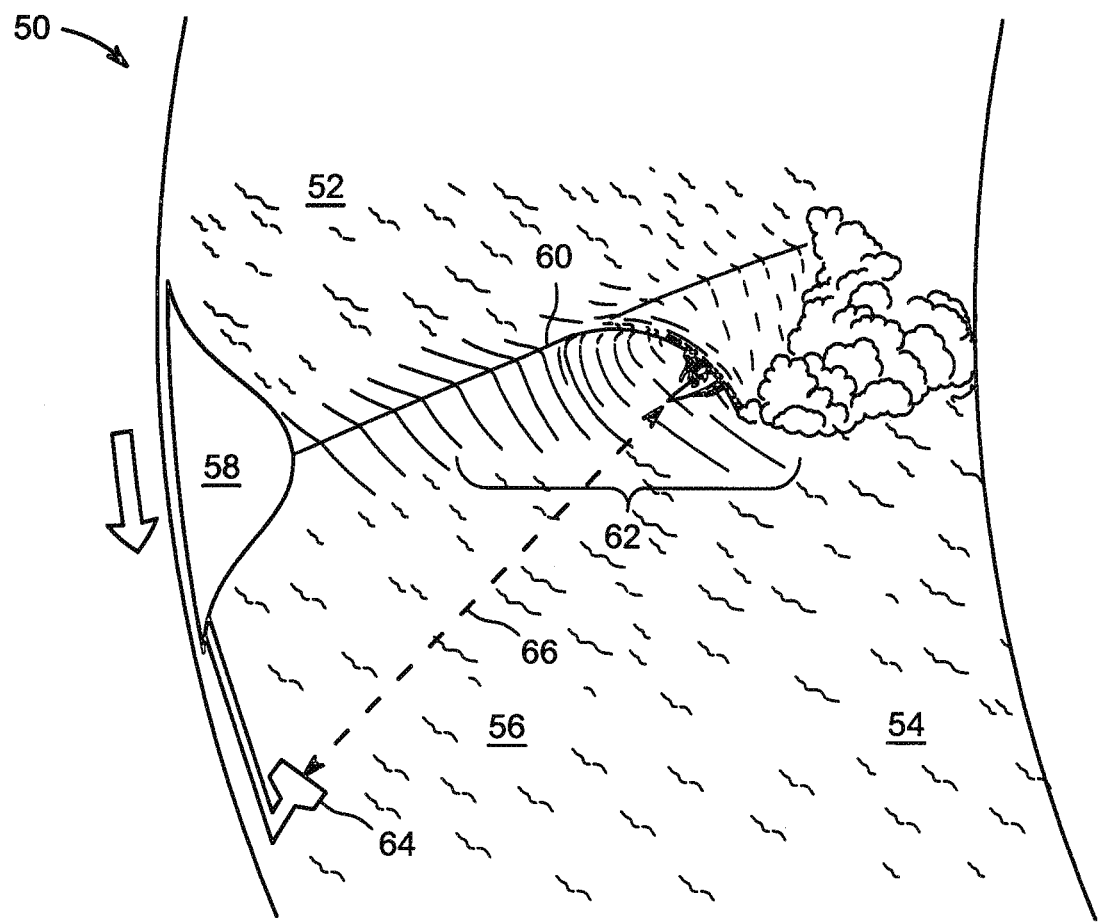
FIG. 1B depicts an apparatus for providing training to a surfer by providing sensory cues while surfing in a pool having a circular motion wave generation mechanism, according to one or more embodiments.

FIG. 1B illustrates an artificial wave generation pool 50, according to various embodiments. The artificial wave generation pool 50 comprises a circular pool 52 of water and an artificial wave generation mechanism (not shown) that generates an artificial wave along the circumference of the pool 52. The pool 52 has a deep region 56 adjacent to a foil 58, which is a part of the artificial wave generation mechanism, and a shallow region 54 adjoining the deep region 16. The shallow region 54 has a base profile with depth that reduces in a direction moving away from the deep region 56 to an inner circumference of the pool 52. The foil 58 is either partially, or fully submerged in water, and as the foil 58 is moved along an outer circumference of the pool 52, water displaced by the foil generates a wave 60, which moves towards the shallow region 54. Similar to the description of FIG. 1A, as the generated wave 60 travels from the deep region 56 to the shallow region 54, the generated wave 60 causes the water to swell, rise, fall on itself generating a 'barrel', and dissipate into foamed water, simulating or replicating waves generated in oceans near a shore. The regions or swell, rise and fall are suitable for surfing and are defined as a surfable region 62. Since the generated wave 60 moves in the same direction as the foil 58, the patterns (such as the surfable region) within the generated wave 60 move along with the generated wave 20 along the length of the pool 52. The foil 58 leads the generated wave 60 and the sections therein, and each section of the generated wave 60 trails the foil 58 within a particular time range, such that the generated wave 60 and portions thereof are synchronized with the movement of the foil 58. According to some embodiments, a sensory cue generator 64 is mechanically coupled to the foil 58, and moves along with the foil 58, while generating sensory cues, in a manner similar to that discussed with respect to the sensory cue generator 24 of FIG. 1A. The sensory cue generator 64 is positioned relative to the surfable region 62 such that the sensory cue generator 64 is in a line of sight 66 from a surfable region of the generated wave 60.

The sensory cue generators 24 and 64 of FIGS. 1A and 1B are coupled mechanically with the foils 18, 58, respectively, and therefore, the movement of the sensory cue generators 24, 54 is automatically synchronized with the respective wave 20, 60. However, other techniques not requiring a mechanical coupling between the sensory cue generators and the foils may be used. In some embodiments, the sensory cue generators 24, 64 are not coupled mechanically to the corresponding foils 18, 58, however, the motion of the sensory cue generators 24, 64 is synchronized according to the motion of the corresponding foils 18, 58. For example, the sensory cue generator (24, 64) is moved at the same time and at the same velocity as that of the foil (18, 58). In some embodiments, the motion of the sensory cue generator (24, 64) is synchronized with the detected motion of the corresponding generated wave (20, 60) or the motion of the foil (18, 58) respectively. The synchronization is achieved by detecting the position of the foil (18, 58) or the generated wave (20, 60) using motion sensors (not shown), pattern recognition techniques, and the like, as are generally known in the art, and moving the sensory cue generator (24, 64) at the same pace as the foil or the generated wave.

While the sensory cue generators (24, 64) of FIGS. 1A and 1B are shown to be above water and in direct line of sight of a surfable portion of the generated wave (20, 60), in some embodiments, the sensory cue generators (24, 64) may be positioned to be under water, for example, lamps to generate light pattern visual cues visible through or on the surf wave to the surfer. In some embodiments, the sensory cue generators (24, 64) may be positioned to deliver sensory cues indirectly in the surfable region to the surfer. For example, light from lamps positioned above water is reflected off the water in the surfable region of the wave (20, 60), and the reflected light is visible in the surfable region to the surfer, providing a visual cue to the surfer. Similar configurations of sensory cue generators may be implemented in various artificial wave generation pools, including the artificial wave generation pools described in U.S. Pat. Nos. 8,366,347, 8,573,887, 8,262,316, U.S. Patent Application Publication 2014/0059758, U.S. Patent Application Publication 2014/0250579, and U.S. Patent Application Publication 2013/0061382, each of which is herein incorporated by reference in its entirety. It is envisioned that in some cases, man-made pools adjoining the ocean may be utilized to harness the waves from the ocean to generate surf waves within such man-made pools, in a relatively isolated environment compared to the ocean, and the techniques described herein may be used by synchronizing a sensory cue generator with the motion of the waves generated in the man-made pool, in a manner similar to that described above.

As used herein, each of the "generated waves" 20 and 60 of FIGS. 1A and 1B respectively, are also referred to as the "surf wave," or an "artificially generated surf wave," unless otherwise apparent from the context. As used herein, the "surfable portion," "surfable region," and "defined surfable region" are used interchangeably, and surfable regions in artificial wave generation pools are regions suitable for surfing by a surfer, and regions in which typically a surfer is expected to surf. The techniques described herein deliver the sensory cues in the surfable region to the surfer, either via a medium which in a line of sight with the surfer (light sources, e.g. lamps, audio speakers, projection lights, including laser projection), indirectly (reflection, underwater lighting) or wirelessly (over electromagnetic medium), and therefore, "delivery position" or the position at which the sensory cue is delivered, generally refers to the surfable region in which the surfer can perceive the sensory cue delivered to the surfing region, unless otherwise apparent from the context. As used herein, "surfboard" encompasses shortboards, longboards, Stand Up Paddle (SUP), SUP Boards, alaiia planks, foilboards, skim boards, boogie boards, body boards, surf mats, bodysurfing handplanes or any other device or piece of equipment designed to aid a human in harnessing and utilizing the energy in waves for sport, recreation, entertainment, leisure, moving meditation, or other purpose. As used herein, "surfing" encompasses the activity popularly known as surfing, and other associated wave riding activities that are referred to as surfing, including all the activities conducted with the aid of the surfboards as described above. As used herein, surfing related "maneuvers" relate to all maneuvers of the body or the equipment while surfing using the surfboard as described above, and includes positioning (both prone on the board and in the surfing area/takeoff spot), paddling, punching through, duck dives, turtle rolls, pulling off, bailing, taking off, dropping in, popping up, bottom turns, top turns, snaps, cutbacks, off-the-lips, re-entries, floaters, aerials, carves, stalls, drags, speed checks, grabs, rotations, trimming, pumping, carving, and of course, barrell riding, also commonly known as "getting so pitted." As used herein, the terms "position" and "location" are used interchangeably, and include orientation unless otherwise apparent from the context. As used herein, the term "synchronous" is used to describe the relationship between a wave generating foil and the surf wave generated thereby, and the term "synchronous" is intended to includes "proportional" or "correlated" relationship, unless otherwise mentioned. As used herein, in some embodiments "while surfing" includes not only surfing a wave in water (physical reality), but also includes "surfing" in augmented reality, and "surfing" virtual reality environments, or in scenarios in which the "surfing" takes place in the mind of the surfer. Accordingly, receiving sensory cues can direct or reprogram the thoughts or visualization practice in the mind of the surfer, which cues can be modified as the surfer progresses in ability. Artificially generated surf wave includes waves in virtual reality or video. Also the surf wave could also be in the mind of the person receiving the sensory cues, in such case the surfing maneuvers would also be performed or enacted in the mind of the surfer. Such mental practice is invaluable in order to improve maneuvers in otherwise dangerous situations in the physical environment. Surfers often visualize maneuvers and mindsets in large, treacherous, or otherwise stressful conditions in order to survive or perform at high levels in such conditions when they are encountered in the natural environment (or competitive scenarios).

Figure 2A:
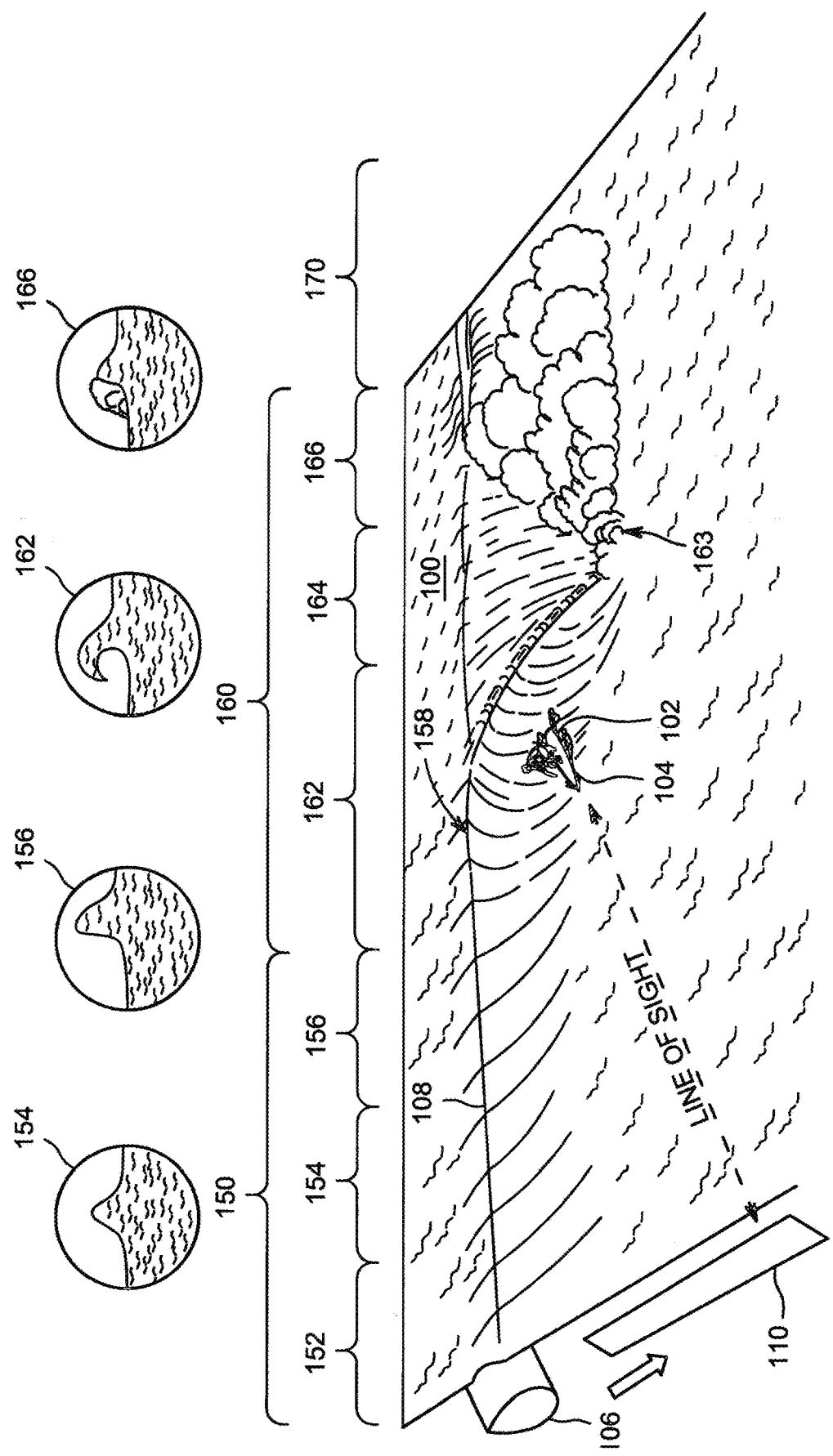
FIG. 2A depicts a surfer surfing in an open barrel section of a surf wave, according to one or more embodiments.

Turning now to FIG. 2A, which depicts a surfer 102 surfing an artificially generated surf wave 108 using a surfboard 104 in a pool 100, according to embodiments of the present invention. The artificially generated surf wave 108, once formed, spans in a diagonal direction across the pool 100, and travels in the direction of motion of a foil 106 (similar to the foil 18 or 58 of FIG. 1A or 1B, respectively). For simplicity of discussion, the surf wave 108 is divided into sections usually seen in artificially generated surf waves. On the left of FIG. 2A is a swell section 150, which comprises a foil swell section 152, which is proximal to the foil 106, respectively. Due to the movement of the foil 106, the water begins to swell in the foil swell section 152, and the swell progresses to sections adjacent to the right of the foil swell section 152. The swell section 150 of the surf wave 108 is divided into a shoulder section 154 in which the water begins to swell or rise further, an escape face section 156 in which the swell has risen further, and is about to develop a lip 158, as illustrated in FIG. 2A.

Next to the shoulder section 156 is the barrel section 160 comprising an open barrel section 162, a closed barrel section 164 and a foamball section 166. In the barrel section 160, the lip 158 is fully developed and plunges forward, continuing the fall to the flat water of the pool 100. The open barrel section 162 is between where the lip 158 begins to form and plunge forward, and the position 163 at which the lip 158 falls on the flat water surface. In the foamball section 166, the falling water on the water surface creates foaming of the water, even though the barrel of the surf wave 108 is intact. To the right of the barrel section 160 is the dissipation section 170, which includes a fully broken section, and diminishing and diminished sections (not shown separately). In the fully broken section, the barrel of the surf wave 108 has been completely filled/consumed with the turbulence of the plunging lip, followed by the diminishing and diminished section, in which the water has dissipated most of its energy, and settles with the rest of the water as the air bubbles formed float to the surface and dissipate into the atmosphere. This is generally a non-surfable region of the surf wave. The circular inset icons 154, 156, 162 and 166 represent the approximate cross sections of the corresponding sections of the surf wave 108.

Figure 2B:
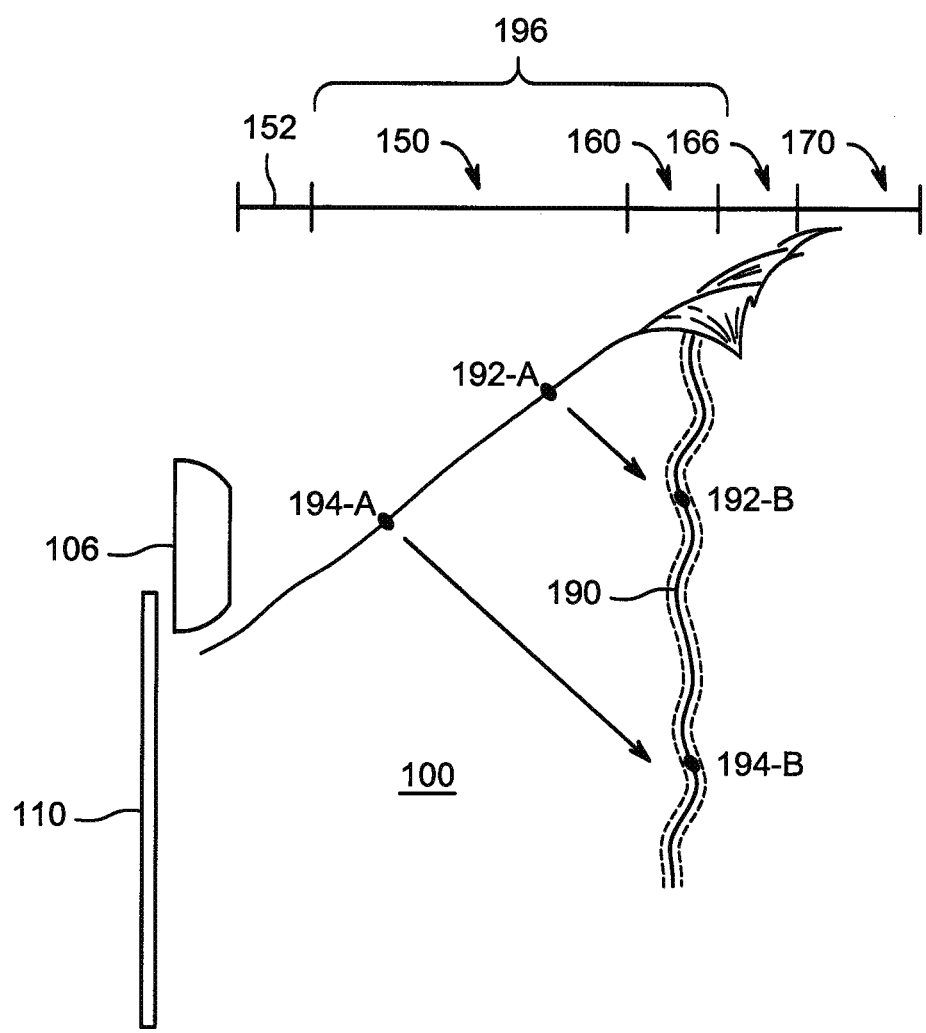
FIG. 2B depicts a top view of an approximate path of the surfer of FIG. 2A riding the surf wave, according to one or more embodiments.

It is noted that FIG. 2A is a side perspective view, facing the surf wave 108 to expose the entire span of the surf wave 108 in similar proportion. However, within the pool 100, the surf wave 108 is led by the foil 106 with the foil swell section 152 on the left hand side, while the diminishing and diminished sections 174 trail the foil 106 on the right hand side, accordingly, the surf wave 108 has a diagonal profile across the pool 100, if viewed from the top. The surf wave 108 maintains its profile depicted in FIG. 2A as it moves through the pool 100, and the foil swell section 152 (and the foil 106) leads the surf wave 108 throughout the pool 100. As the surf wave 108 progresses forward along the length of the pool 100, the profile of various sections 150-176 of the artificially generated surf wave 108 described above is maintained and the sections move forward along the length of the pool, at approximately the same positions in a lateral direction across the pool 100. The surfer's motion is dynamic, and includes generally sinusoidal movements on the face of the artificially generated surf wave 108, in which the surfer pumps up and down on the face of the surf wave. Even within the generally sinusoidal motion, the surfer's movements are multi-dimensional, including minor yaw, rotation, and other similar movements. Since the surf wave 108 maintains its profile as it moves along the length (or the curve) of the pool 100, the surfable portion moves along and parallel to the length (or along a curve) as well. For example, FIG. 2B depicts a top view of a surfer's sustained surfing motion along a surfer's path 190 in a surfable region 196 of the surf wave 108 in the pool 100. Various positions 192-A and 194-A on the surf wave 108 are projected to traverse to positions 192-B and 194-B respectively such that the energy transfer from a swell portion of 192-A, 194-A becomes a barrel 192-B and 194-B with passage of time, along with the motion of a wave generating foil, for example, similar to the foil 18 of FIG. 1A. The relation between the points 192-A, 194-A and 192-B, 194-B also depicts the synchronous relationship between motion of the foil 106 and motion of the surf wave 108.

The surfable region 196, which comprises the swell section 150 and the barrel section 160 described in FIG. 2A, is suitable for surfing because surfers tend to stay between the shoulder section 154 of the swell section 150 and the closed barrel section 164 of the barrel section 160 to maximize their surf time. Although surfers may stray close to the foamball section 166, surfers maneuver back to the closed barrel section 164, for example, based on receiving a sensory cue from a sensory cue generator 110 synchronized with the motion of the foil 106 and the surf wave 108, for example, as described above. In such arrangements, typically, the surfer's 102 orientation is to face generally towards the foil 106 (towards left in FIG. 2A) or the foil swell section 152. In the illustration of FIG. 2A, a sensory cue generator 110 is positioned and oriented facing the anticipated position and orientation of the face of the surfer 102 surfing the surf wave 108, to provide a line of sight from the surfer 102 to the sensory cue generator 110, and vice-versa. According to some embodiments, the sensory cue generator 110 is positioned ahead of the foil 106 in the direction of motion of the foil 106. According to some embodiments, the sensory cue generator 110 is stationary and extends along the length or the circumference of the pool 100, and is activated in portions that have a line of sight from the surfer 102 surfing the surf wave 108. In some embodiments, surfers may face a different predetermined direction or a direction range, and the sensory cue generator 110 is positioned accordingly to be oriented to face the surfer while surfing in the surfing region.

Figure 2C:
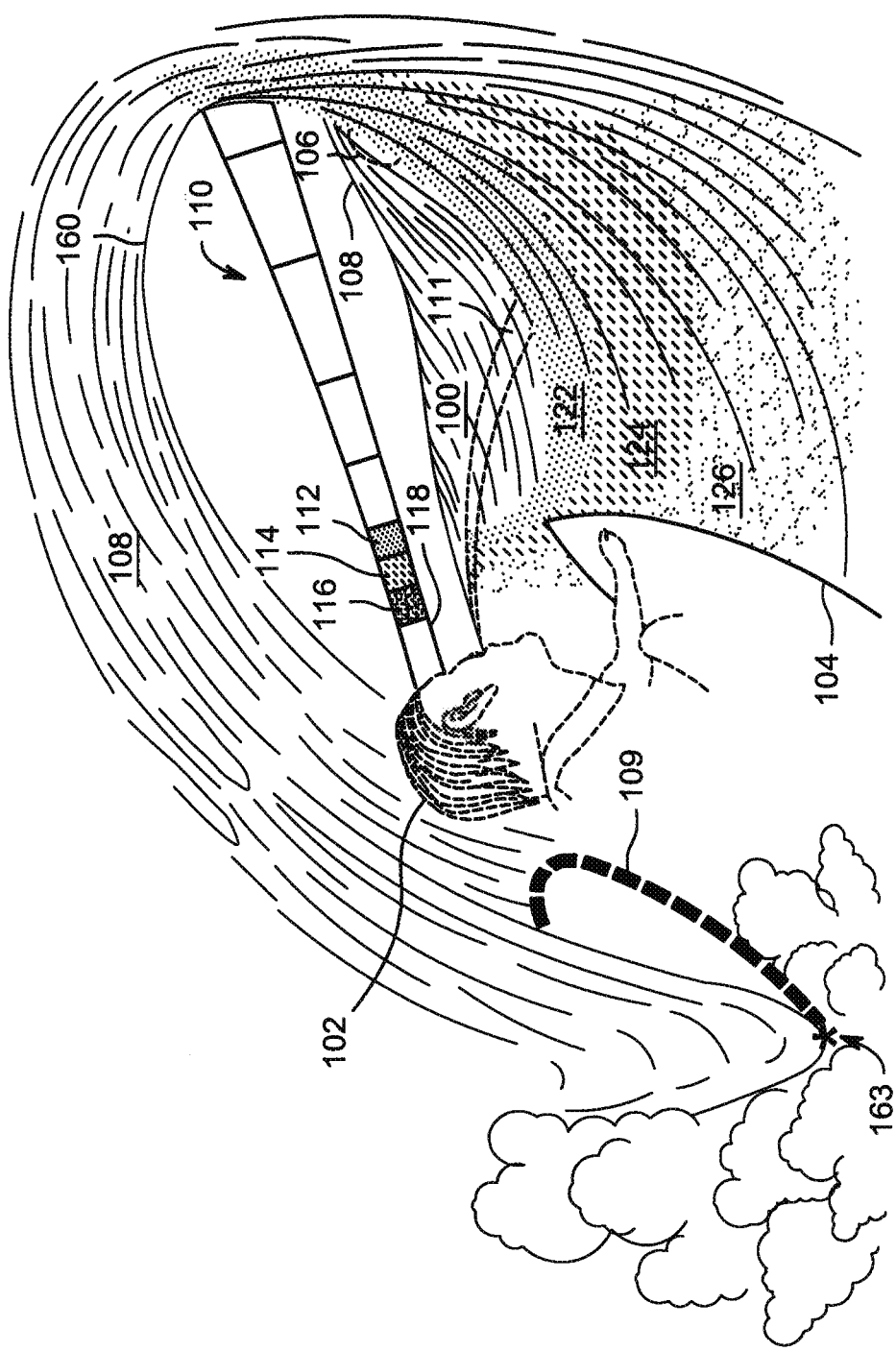
FIG. 2C depicts a surfer sensing the sensory cues while surfing in a barrel section of a surf wave, according to one or more embodiments.

FIG. 2C depicts a surfer's view while the surfer 102 is surfing the surf wave 108, according to some embodiments. The surfer 102 surfs the surf wave 108 using a surfboard 104. The surfer 102 has surfed to a position in the barrel section 160 as discussed with respect to FIG. 2A, and is surfing on the surf wave 108 moving along the pool 100, as shown in FIG. 2B. The surfer 102 has a line of sight to sensory cue generator 110, which comprises multiple lights 112, 114, 116, and 118. The lights 112, 114 and 116 are illuminated while the lights 118 are not illuminated. In some embodiments, the lights 112, 114, 116 are illuminated in a pattern that is visible to the surfer 102 and indicates to the surfer to maneuver the surfboard 104 and his/her body to turn right. For example, the lights 112, 114, 116 may illuminate in the form of an arrow pointing right, or illuminate as a text displaying "RIGHT," or any other predefined representation pattern of the cue. In some embodiments, lights 112, 114, 116 are individual light lamps, and lamps 114, 116 light up yellow, while lamp 112 (which is the right most of the illuminated lamps) lights up green. Upon registering (seeing) the visual cue, the surfer 102 may then deploy the maneuver to move towards the right, as indicated by the sensory cue generator 110.

In some embodiments, sensory cues are the reflection of light on the surf wave 108 visible to the surfer 102, for example, reflections 122, 124 and 126 of the lights 112, 114 and 116, respectively, generated on the surface of the surf wave 108. The reflected light patterns 122, 124 and 126 alone or in combination form a visual cue for the surfer 102 to deploy a surfing maneuver. For example, in FIG. 2C, the different shading illustrates that lights 112 are illuminated green, causing a green reflection 122 on the surf wave 108. Similarly, light 114 and its reflection 124 are yellow, while the light 116 and its reflection 126 are red. By a predetermined scheme made available to the surfer, the surfer 102 is aware that he/she needs to maneuver onto the apparent path created by the reflection 122 of the green light, and therefore, the surfer 102 maneuvers by pumping up, facing away from the breaking lip, to position to trim to the path depicted by the sensory cue of the green reflection 122, effectively "following the light," According to some embodiments, the lights 112, 114 and 116 are configured to generate light such that the reflected light pattern 122, 124 and 126 formed on the surf wave 108 indicate a path on which the surfer should maneuver. For example, light 112 is illuminated green, and/or in a shape such that its reflection 122 on the surf wave 108 projects a path 122 in green, indicating to the surfer 102 to maneuver to trace the reflection 122. The lights 114 and 116 may be illuminated in yellow or red colors to generate corresponding yellow and red reflection 124, 126 to indicate that maneuvering to such regions is undesirable. The profile of face of the surf wave 108 creates a curvilinear reflection of light visible to the surfer, for example as seen by the reflection patterns 122, 124 and 126, or reflection 111 of the entire sensory cue generator 110 that comprises the lamps 112, 114, 16 and 118. Similarly, the curve illustrated by line 109 illustrates a path on the surface of the pool 100, where the lip of the surf wave 108 will impact the flat water surface as the surf wave 108 breaks in a continual progression into the pool 100 over time. For a constant bathymetry, the curve 109 represents a path parallel to the motion of the foil 106, and the reflection 111, and/or the sensory cue generator 110. Further, the area immediately adjacent to the line 109 represents the bottom terminus of the surfable portion of the open barrel, and is therefore a useful guide for the designation of the surfable region inside the barrel. The line 109 may be made visible to the surfer as sensory cue in a manner similar to the sensory cue 122 generated by reflecting green light. In some embodiments, the sensory cues recommend the surfer 102 to utilize his or her position on the face of the surf wave to use gravity to accelerate down the face of the surf wave, as close as possible to the line 109 in order to maximize the potential of the wave.

As seen in FIG. 2C, according to some embodiments, the illumination patterns of lights 112, 114 and 116 are shifted in the direction of the motion of the surf wave 108, to stay synchronized with the movement of the surf wave 108 on which the surfer 102 is surfing. This synchronization may be achieved by illuminating a next or consecutive set of lights in the same patterns as the lights 112, 114, 116. For example, as the surfer 102 moves along the surf wave 108, generally towards left in FIG. 2C, the line of sight correspondingly shifts in the direction of motion of the surf wave 108. Accordingly, the light 118 ahead of light 116 is illuminated in the pattern generated by the light 116, the light 116 is illuminated in the pattern generated by the light 114, the light 114 is illuminated in the pattern generated by the light 112, and the light 112 is turned off. Illuminating lights in this manner provides one or more sensory cues generated by the lights 112, 114, 116 moving along with the surf wave 108 to the surfer.

While the embodiments discussed above describe generation and delivery of sensory cues according to synchronization with the motion of the foil 106 or the surf wave 108, in some embodiments, the location of the surfer 102 or the surfboard 104 is also accounted for, to enable more accurate sensory cues, and more accurate delivery of such sensory cues.

Figure 3A:
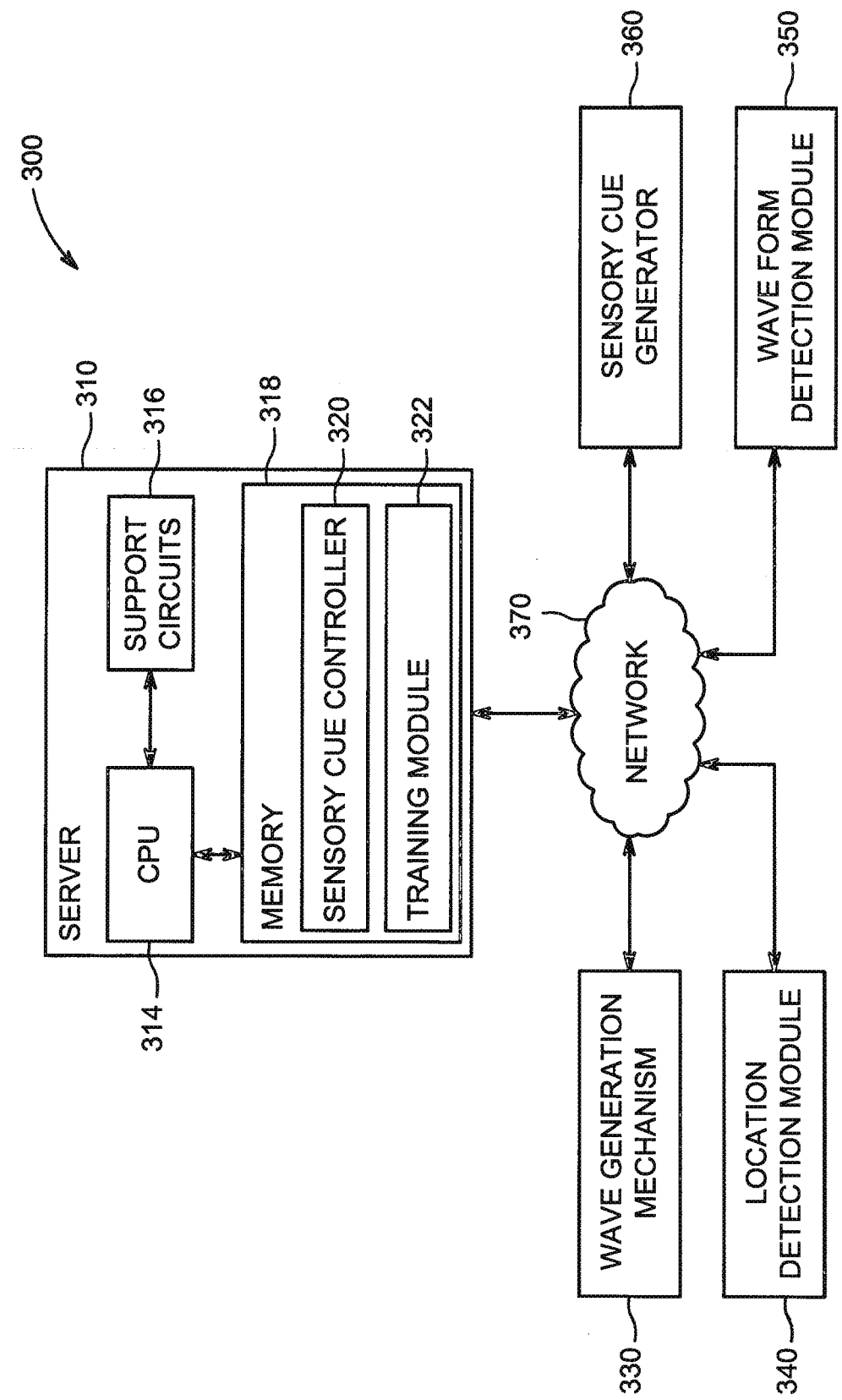
FIG. 3A depicts an apparatus for providing training to a surfer, according to one or more embodiments.

FIG. 3A depicts a schematic illustration of a surfer training apparatus 300, according to some embodiments of the invention. The apparatus 300 comprises a server 310, a wave generation mechanism 330, a location detection module 340, a waveform detection module 350, a sensory cue generator 360, and a network 370 for enabling communication between one or more components of the apparatus 300.

The server 310 may be a computer, laptop, tablet, or any other digital processing device as generally known in the art. The server 310 comprises a CPU 314, support circuits 316, and a memory 318 containing instructions and algorithms. The CPU 314 processes inputs and outputs to the server 310. The CPU 314 may be any commercially available digital processor, microprocessor, microcontroller, and the like. The support circuits 316 comprise well-known circuits that provide functionality to the CPU 314 such as a user interface, clock circuits, network communications, cache, power supplies, I/O circuits, and the like. In some embodiments, the user interface comprises a keypad, electronic buttons, dials, speaker, touchscreen, display, or other user interaction mechanism for programming or otherwise operating the server 310. Alternative embodiments may use control algorithms on a custom Application Specific Integrated Circuit (ASIC) to implement the functionality afforded by the CPU 314, the support circuits 316, and the memory 318.

The memory 318 may be any form of digital storage used for storing data and executable software or programming instructions. The memory 318 includes, but is not limited to, random access memory, read only memory, disk storage, optical storage, and the like. The memory 318 stores computer readable instructions corresponding to an operating system (not shown), a sensory cue controller 320, and a training module 322.

The sensory cue controller 320 instructs the sensory cue generator 360 to generate sensory cues based on one or more of location of the surf wave, location of the wave generating foil, location of the surfer and/or the surfboard on the surf wave, a predefined path for surfing the surf wave, or a repository of surfing maneuvers. The sensory cue controller 320 determines the location of the surf wave based on input received from the wave generation mechanism 330, or input received from the waveform detection module 350, or both. Location of the wave generating foil (e.g. the foil 106 of FIGS. 2A-2C) is communicated by the wave generation mechanism 330 to the sensory cue controller 320.

The sensory cue controller 320 determines the location of the surfer or the surfboard based on input received from the location detection module 340. The location detection module 340 includes global positioning (GPS) sensors, electromagnetic wave signal strength triangulation (e.g. using cellular signals, Bluetooth, WiFi, among other known techniques) sensors paired with a corresponding sensor worn by the surfer and/or attached to the surfboard. For example, the surfer may have one or more of a smartphone, a wearable watch, anklet or other position identifying sensors worn on the surfer's body while surfing. The devices worn by the surfer may generate and transmit location data (GPS, Bluetooth, WiFi, cellular signals) to the sensory cue controller 320. In some embodiments, the surfer further wears multiple sensors on different body parts to identify the motion of the corresponding body part, thereby capturing the body motion form of the surfer while surfing. The location detection module 340 therefore captures the location of the surfer and/or the surfboard and/or the body form of the surfer and communicates it to the sensory cue controller 320. In some embodiments, the location detection module 340 communicates an aggregated path of the surfer while surfing the surf wave, where the path includes location information of the surfer and/or the surfboard to enable recreation of the path taken by the surfer while surfing the surf wave.

The sensory cue controller 320 receives a predefined recommended path for surfing the surf wave from the training module 322. The training module 322 comprises a repository of surfing maneuvers, for example, as commonly implemented by surfers. The training module 322 also comprises a repository of surfing conditions indexed to specific surfing maneuvers, identifying surfing maneuvers typically employed or recommended in a given condition. The surfing conditions include information regarding the wave (e.g. parameters such as the height, period (or artificially generated equivalent metric correlated with potential energy), peel angle, steepness, velocity, height, "heaviness", surface texture (choppy, glassy, soglassy) and the like), and information regarding the surfer and/or the surfboard (e.g. velocity, power, flow, orientation relative to previous performance, ideal position, and the like). Based on the location of the wave and location of the surfer and/or the surfboard on the surf wave, the sensory cue controller 320 identifies, using the repository of surfing maneuvers and/or the repository of surfing conditions, at least one surfing maneuver to recommend to the surfer. For example, as a surfer is riding a wave and approaching a section that will barrell, the waveform recognition module 350 recognizes that the wave is about to create an open barrelling section and recommends that the surfer bottom turn, stall and position to trim in the correct portion of the face as the wave begins to barrell. Once a surfing maneuver is identified, the sensory cue controller 322 sends a signal to the sensor cue generator 360 to generate the appropriate sensory cue. As discussed above, the sensory cues include one or more of light and light patterns, sounds, touch-based cues. In some embodiments, taste, smell or breathing pattern based cues may also be deployed. A combination of one or more such cues may be utilized to guide the breathing patterns associated with both physical and mental states.

Figure 3B:
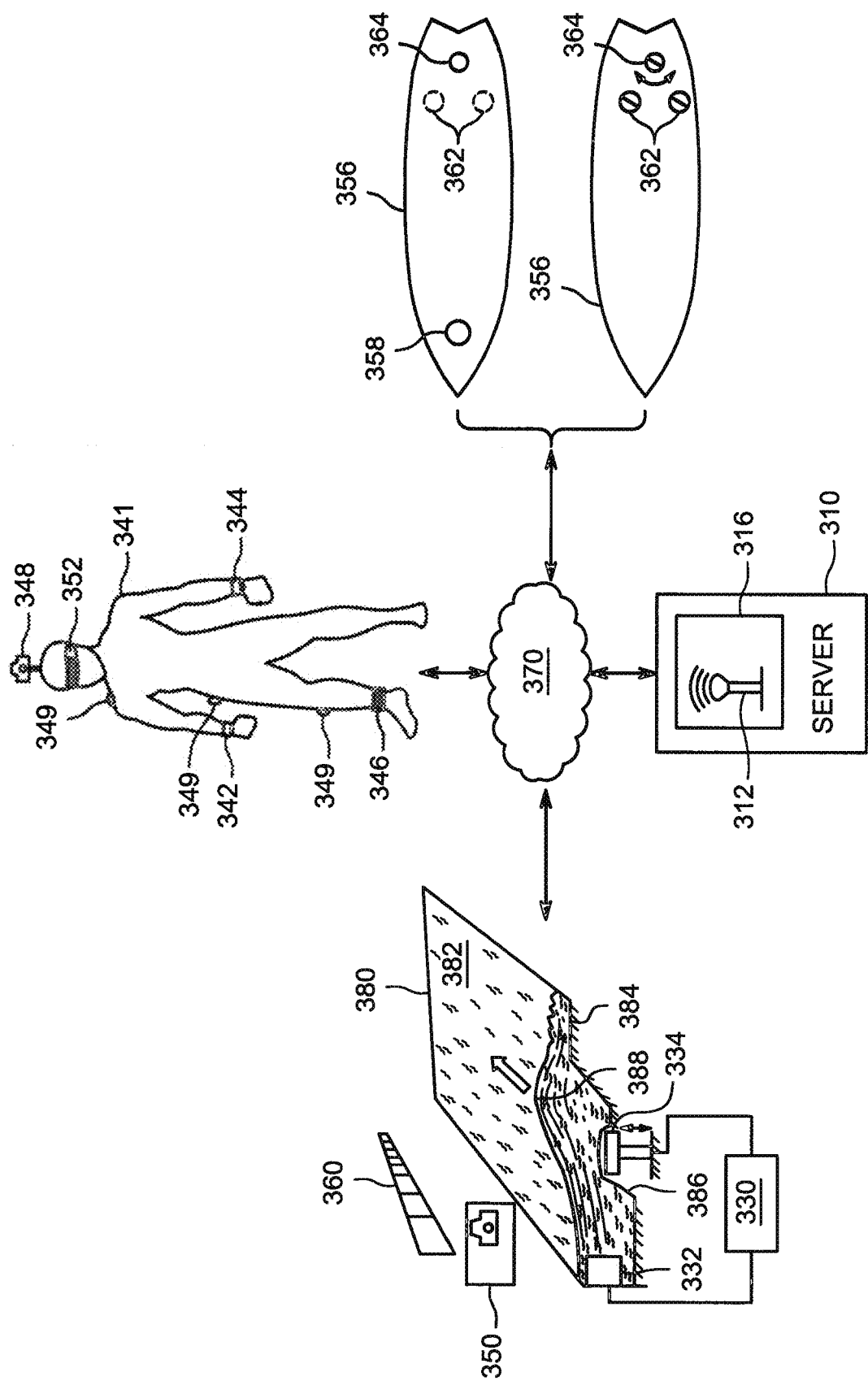
FIG. 3B depicts elements comprised in the apparatus of FIG. 3A, according to one or more embodiments.

FIG. 3B depicts some of the elements comprised in the apparatus of FIG. 3A, according to some embodiments of the invention. For example, the server 310 comprises support circuits 316, which in turn comprise a transceiver 312 to send and receive information with other components of the apparatus 300.

The wave generation mechanism 330 includes a wave generating foil 332, for example, similar to foil 106 described in FIGS. 2A-2C and a bathymetry modifier 334 installed in a pool 380. The bathymetry modifier 334 modifies depth of a portion 386 of a base 384 of the pool 380. In addition to the motion of the foil 332, the bathymetry as modified by the bathymetry modifier 334 also impacts the motion, and profile of the surf wave 388 generated by the wave generation mechanism 330. The wave generation mechanism 330 also includes other components (not shown), for example, a first driver to drive the foil 332, a second driver to drive the bathymetry modifier 334, a controller to control the first and second drivers, among others. The wave generation mechanism 330 communicates the wave generation data, for example, the foil position, foil velocity, and bathymetry to the sensory cue controller 320 via the network 370.

The waveform detection module 350 comprises of an image capture device, such as a still or a motion camera, motion sensor or laser based detection system, such as LIDAR, positioned to capture an image or other pattern recognition data of a surf wave 388 generated in the pool 380. The waveform detection module 350 further comprises pattern recognition modules that identify the location of the surf wave 388 in the pool 380 based on the image captured the still or motion camera, or on data captured by the the LIDAR system.

FIG. 3B illustrates various components of the location detection module 340 worn by a surfer 341, and installed on a surfboard 356. The surfer 341 has a smartphone 342 (or another smart device) capable of capturing location using GPS, and/or of wireless radio communications. The surfer 341 may strap the smartphone to the surfer's body via a strap holder (not shown). Similar to the smartphone 342, the surfer 341 further wears a bracelet 344 and/or an anklet 346 capable of capturing location using GPS, and/or of wireless radio communications, and generating vibrations to provide a touch based cue to the surfer 341. The surfer 341 may also wear a camera 348, for example GOPRO cameras, 360FLY cameras, to capture still, video including spherical or virtual reality capable video, of the surfing experience, and a virtual/augmented reality wearable 352 over the surfer's eyes to deliver sensory cues to recommend a surfing maneuver to the surfer 341. The surfboard 356 has conventional fins 362 on the bottom surface of the surfboard 356. The surfboard 356 includes an attached device 358 capable of capturing location using GPS, and/or of wireless radio communications, and further includes a transducer or a motor to generate a vibration on the surfboard 356 to provide a touch based sensory cue to the surfer 341 when riding the surfboard 356. The surfboard 356 also includes at least one rotatable fin 364, which is mounted on a motor that rotates the fin 364 based on receiving a signal from the server 310, the smartphone 342 or any other module of the apparatus 300. In some embodiments, the surfer 341 wears a mask, nasal or oral regulator (not shown) to capture data regarding the surfer's 341 respiration patterns, gas exchange efficiency, and the like for the purposes of analyzing the surfer's training and recommending improvements.

In some embodiments, the network 370 includes one or more networks including but not limited to Local Area Networks (LANs) (e.g., an Ethernet or corporate network), Wide Area Networks (WANs) (e.g., the Internet), wireless data networks, cellular networks, Wi-Fi, Bluetooth, or some other electronic data communication network, or a combination thereof. In some embodiments, the network 370 includes a point to point wired or wireless communication between one or more components of the apparatus 300, for example, as illustrated with respect to FIGS. 3A and 3B.

In some embodiments, the training module 322 also comprises a library of one or more recommended paths for surfing the surf wave 388. Such recommended paths include, for example, surfing paths of one or more experts when surfing a surf wave in the pool 380 generated by the wave generation mechanism 330. Experts or surfing enthusiasts may capture their surfing paths on the surf wave 388, recorded using the location detection module 340, for example, and surf paths may be used to generate sensory cues for the surfer 341 to emulate such pre-recorded paths when surfing the surf wave 388. A learning surfer may similarly record his or her surfing path from a surfing session for later analysis, and store the surfing path to the training module 322. The surfing path stored in the training module 322 may then be used at a time the learning surfer is not surfing, to visualize the surf path of the surfing session for training purposes. In some embodiments, the surf path is combined with a recording of the surfing session, for example, captured using the camera 348, and displayed on a digital display screen, such as a television or an augmented screen or a virtual reality screen for convenient visualization and learning. While visualizing such surf path for the purposes of training, the sensory cue controller 320 generates notes for the surfer indicating recommended surfing maneuvers for the surfing path taken by the surfer in the surfing session. In some embodiments, the surfer modifies his or her surf path while visualizing the surf path for training, and the modified surf path is usable for the surfer when surfing, and wherein the apparatus 300 generates and delivers sensory cues to the surfer, enabling the surfer to maneuver according to the modified surf path created by the surfer during visualization. Further, the surf paths stored in the training module 322 can be shared via the network 370, for example, the Internet, for research, analysis, or as a social communication. In some embodiments, the training module 322 can access surf paths, such as those of experts, or those implementing specific maneuvers, stored in a repository connected to network 370, for example, for a subscription fee. Similarly, access to the surf paths stored in the training module 322 may be requested by others, and such access may be granted based on an access fee or other criterions established by the surfer.

Figure 3C:
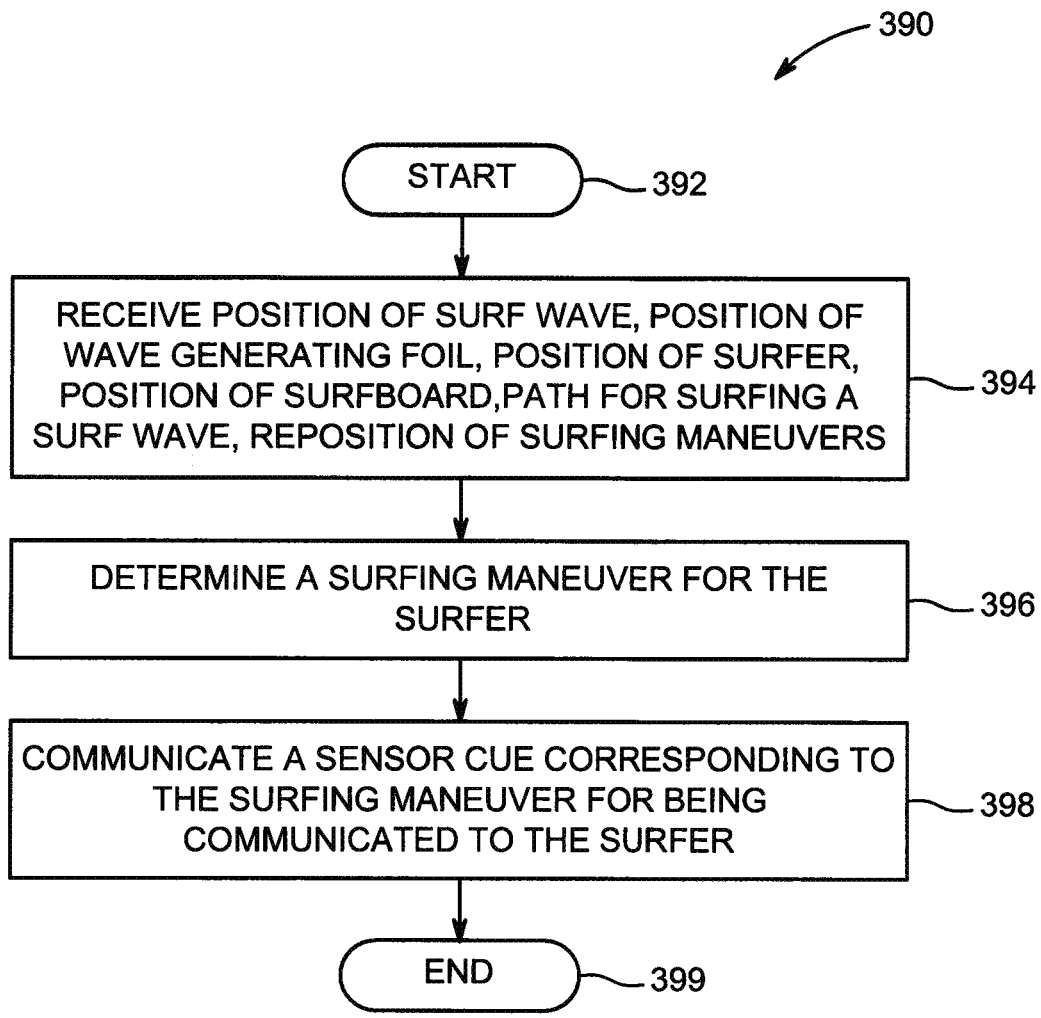
FIG. 3C depicts a method for providing training to a surfer, according to one or more embodiments.

FIG. 3C depicts a flow diagram of a method 390 for generating a sensor cue, according to embodiments of the inventions. The method 390 begins at step 392, and proceeds to step 394 at which the sensory cue controller receives at least one of position of the surf wave, position of a wave generating foil, position of the surfer, position of a surfboard being used by the surfer for surfing the surf wave, a predefined recommended path for surfing the surf wave, or a repository of surfing maneuvers. Position of the surf wave is determined from an input from the wave generation mechanism 330 or a waveform detection module 350, or calculated in the manner described below.

As discussed above, motion of the surf wave is correlated with the motion of the wave generating foil, and therefore the location of the surf wave is determinable based on the time the wave generating foil started moving, and the velocity of the wave generating foil. For example, if it is known that the wave generating foil is moved at a steady velocity, and the barrel of the surf wave is generated approximately 10 seconds after the wave generating foil begins moving, then it can be determined that the barrel will always trail the wave generating foil by 10 seconds at a given lateral position in the pool, provided the velocity of the wave generating foil remains constant. Further, different parameters of wave generation, for example, foil velocity, surf wave velocity, bathymetry profile, height or profile of various sections of the surf wave, and other parameters may be correlated for a given pool. Thereafter, for a given set of known parameters, one or more unknown parameters can be calculated in real time based on interpolating or extrapolating the known parameters. For example, if it is known that for a given bathymetry and foil velocity of 5 miles an hour, the maximum surf wave height is 7 feet, and for the same bathymetry and foil velocity of 7 miles an hour, the maximum surf wave height is 9 feet, then for the same bathymetry and foil velocity of 6 miles an hour, the maximum surf wave height is calculated to be 6 feet. While an example of simple interpolation is provided, those skilled in the art would readily appreciate application of more accurate mathematical techniques to calculate unknown parameters based on known parameters for a given pool, and for example, as referenced in the U.S. Pat. No. 8,262,316. In this manner, the sensory cue controller 320 conducts such and similar calculations to determine the position of the surf wave based on the position of the wave generating foil and/or other wave generation parameters.

The position of the surfer and/or the surfboard is provided by the location detection module 340. Communication from various devices described in FIG. 3B include GPS location signals, cellular phone triangulation location signals, other communication signals such as WiFi, bluetooth that may be used to determine the location of the devices, and thereby, location of the surfer and/or the surfboard, using known techniques.

The method 390 proceeds to step 396 at which the sensory cue controller 320 analyzes the location of the surf wave and the location of the surfer and/or the surfboard, and determines by consulting the repository of surfing maneuvers and the repository of surfing conditions from the training module 322, one or more surfing maneuvers to recommend to the surfer.

The method 390 proceeds to step 398 at which the sensory cue controller 320 communicates a sensory cue corresponding to the one or more surfing maneuvers to the sensory cue generator 360 for being communicated to the surfer while surfing the surf wave 388. In some embodiments, the sensory cue controller 320 communicates the surfing maneuvers to a display on which a surfer is visualizing a previously surfed surfing session for training purposes. The method 390 proceeds to step 399, at which the method 390 ends.

In some embodiments, an expert or a coach of the surfer may manually control the delivery of sensory cues generated by the method 300, to the surfer. The expert or coach may determine how much assistance of sensory cues the surfer needs, based on which the coach may selectively turn on or off the delivery of sensory cues to the surfer. In some embodiments, the expert or the coach updates the training module 322 to include one or more additional maneuvers or surf paths. In some embodiments, the expert or the coach decides whether the automatically generated sensory cue corresponding to and recommending a maneuver is prescribed for the surfer or not, based on which the expert or the coach prevents or allows the delivery of the corresponding sensory cue. In some embodiments, an artificial intelligence (AI) and/or a machine learning (ML) algorithm is included as a part of the programming of the server 310, and more particularly the sensory cue controller 320 and/or the learning module 322. In such embodiments, the method 300 learns over time, from expert surf paths, from coach assisted sessions and several other known AI/ML techniques, and is able to generate sensory cues for a learning surfer similar to an expert or coach. For example, the AI/ML algorithms, or other custom algorithms determine potential outcomes of a surfing maneuver, within the limits of the laws of physics, and based on knowledge of known data pertaining to a surfer's range of motion, strength, equipment capabilities and the wave. In this manner, the method 300, using various known algorithm and programming techniques prescribes specific maneuvers or a set thereof generating a training program, for improving a surfer's performance. For example, if what laws of physics allow for a particular surfing maneuver is considered a 100%, an expert's relative performance may be measured at about 98%, and a surfer's performance may be measured at 63%. The method 300 may, based on the comparison of the surfer's body type, fitness levels, age may determine that the surfer is performing at about 80% of his or her potential, and recommends surf path or surf plan comprising maneuvers to help the surfer improve by the next 1%.

Figure 4A:
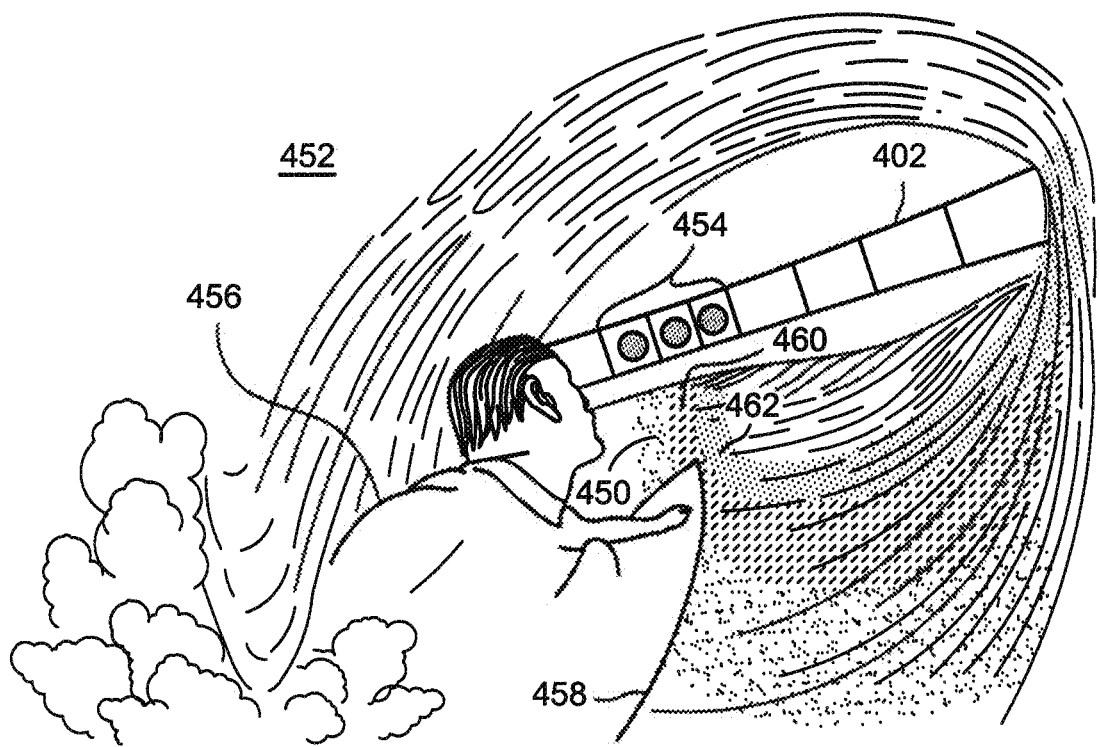
FIGS. 4A-4G depict various types of sensory cues provided to a surfer, according to one or more embodiments.
Figure 4B:
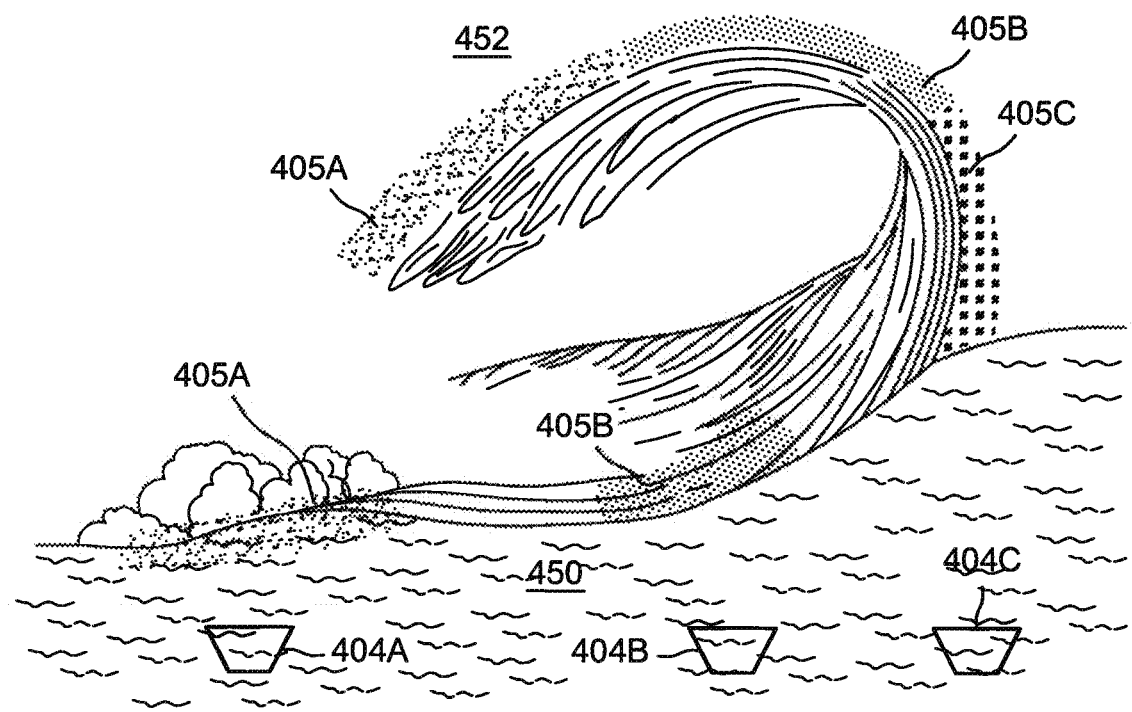
Figure 4C:
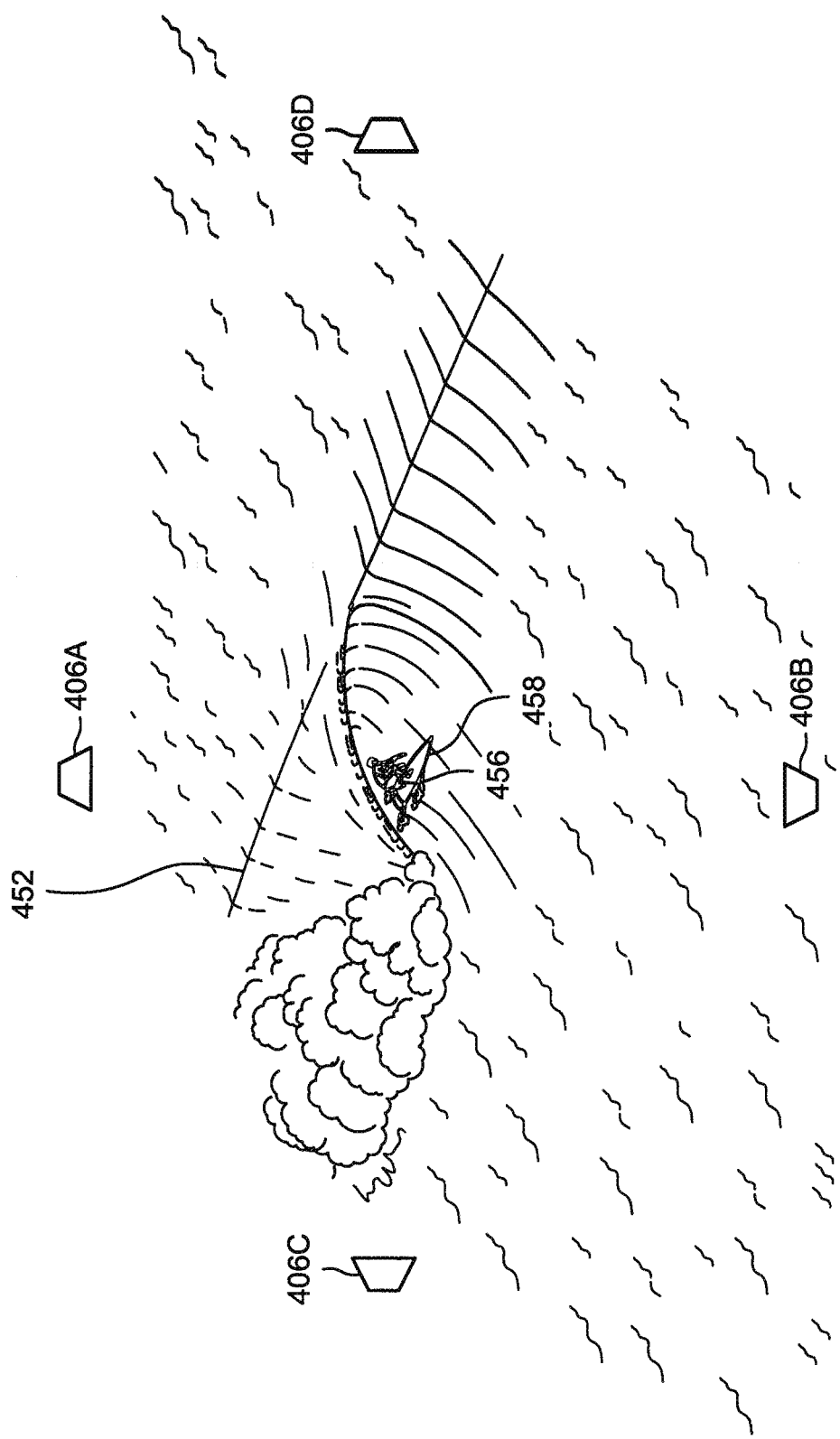

FIGS. 4A-4F depict the delivery of the sensory cues, for example the sensory cues generated by the apparatus 300 and the method 390, to a surfer 456 while surfing in a pool 450 using a surfboard 458. FIGS. 4A, 4B, and 4D-4F depict a surf wave 452 that the surfer 456 is surfing, and represents a cross section of the barrel of the surf wave 452 looking out of the barrel. FIG. 4C depicts the surfer 456 surfing surf wave 452 from a top perspective view. Turning now to FIG. 4A, a sensory cue generator 402 comprising lamps 454, illuminates the lamps 454 based on a sensory cue signal received from, for example, the sensory cue controller 320 of FIG. 3. In some embodiments, the illumination pattern of the lamps 454 is the sensory cue delivered to the surfer 456, for example, in a manner similar to the illustration of FIG. 2C. In some embodiments, reflection patterns 460, 462, 464 made by light reflecting from the lamps 454 is the sensory cue delivered to the surfer 456, for example, in a manner similar to the illustration of FIG. 2C. In some embodiments, the pattern 462, which corresponds to the pattern 122 of FIG. 2C, represents a recommended path for the surfer 456 to follow or trace while surfing.

FIG. 4B depicts the surf wave 452, and underwater lamps 404A, 404B and 404C which comprise the sensory cue generator. The lamp 404A is positioned directly underneath where a foam ball section and/or a fully broken section of the surf wave 452 forms. Since foamball section (and all other sections of the wave) trace a region in the pool 450 parallel to the wave generating foil, multiple lamps 404A are installed in the region where the foamball section is expected to be formed. The lamp(s) 404A generate a light pattern 405A in the foramball section and the fully broken section. For example, upon receiving a sensory cue signal, the lamps 404A generate a red light, illuminating the foamball section and the fully broken section in red color, generating an appearance of a red foam, which is visible to the surfer 456, the red color communicating that it is undesirable to surf towards this region or allow this region of the wave to overtake one's position as the wave continuously peels. Similarly, one or more lamps 404B are positioned directly underneath the barrel section of the surf wave 452, and the region in the pool 450 in which the barrel section is expected to be formed. According to some embodiments, the lamp(s) 404B generate green light forming a green pattern 405B on the surf wave 452, is visible to the surfer 456, the green color communicating that it is desirable to surf and stay in this region, maneuvering to oppose surfing conditions that may cause the surfer to move out of the green region. Similarly, one or more lamps 404C are positioned in an offset to lamps 404B to illuminate the barrel from the outside, and the lamps illuminate the opposing side of the barrel in pattern 405C, which is visible to the surfer 456.

FIG. 4C depicts a top view of the surf wave 452 in the pool 450, and lamps 406A, 406B, 406C and 406 D installed over water, which comprise the sensory cue generator. The lamp 406A is installed at an overhead position, the lamp 406B is installed generally facing the surf wave 452, the lamp 406C is installed proximal to the diminishing and diminished sections of the surf wave 452, and the lamp 406D is installed proximal to the foil swell section of the surf wave 452. Upon receiving a sensory cue signal, one or more of the lamps 406A, 406B, 406C or 406 D are illuminated in a different colors, intensity, sequence, or a combination thereof, which generates a light pattern visible to the surfer 56 while surfing, thereby communicating the visual sensory cue to the surfer 456.

Figure 4D:
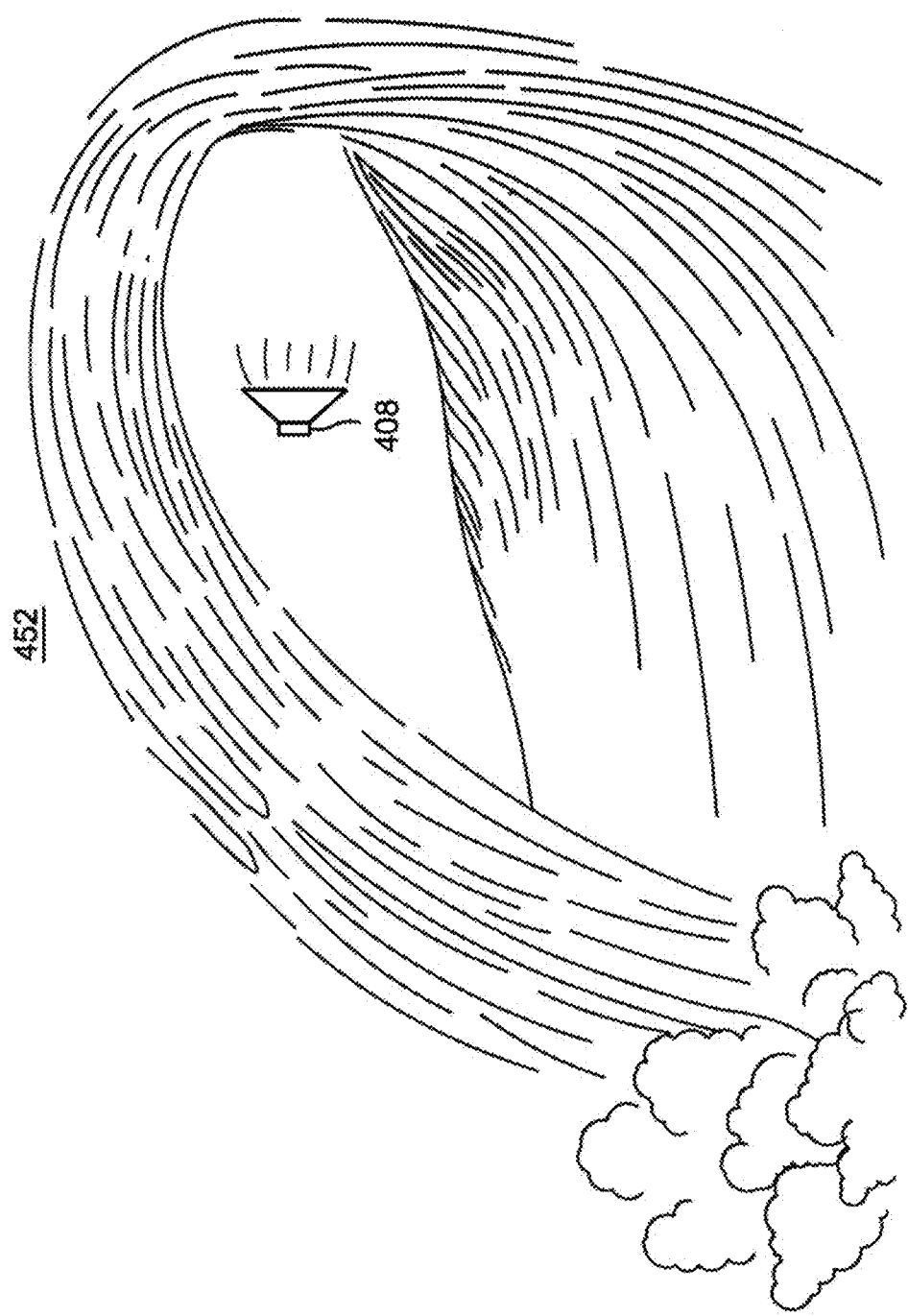

FIG. 4D depicts the surf wave 452, and one or more audio speakers 408, which comprises the sensory cue generator. Upon receiving a sensory cue signal from the sensory cue controller 320, the audio speakers 408 generate one or more sounds of varying intensity (loudness), pitch, frequency, sequence, or a combination thereof, which is audible to the surfer 456 while surfing the surf wave 452. The sound communicates the sensory cue to the surfer. In some embodiments, the sensory cue is a buzzer like sound generated by the audio speaker(s) 408 to indicate that the surfer 456 is surfing towards the foamball section. In some embodiments, the sensory cue is a human voice pattern generated by the audio speaker(s) saying, for example, "move left" to indicate to the surfer 456 to maneuver towards left in order to stay on a suitable portion of the surf wave 452.

Figure 4E:
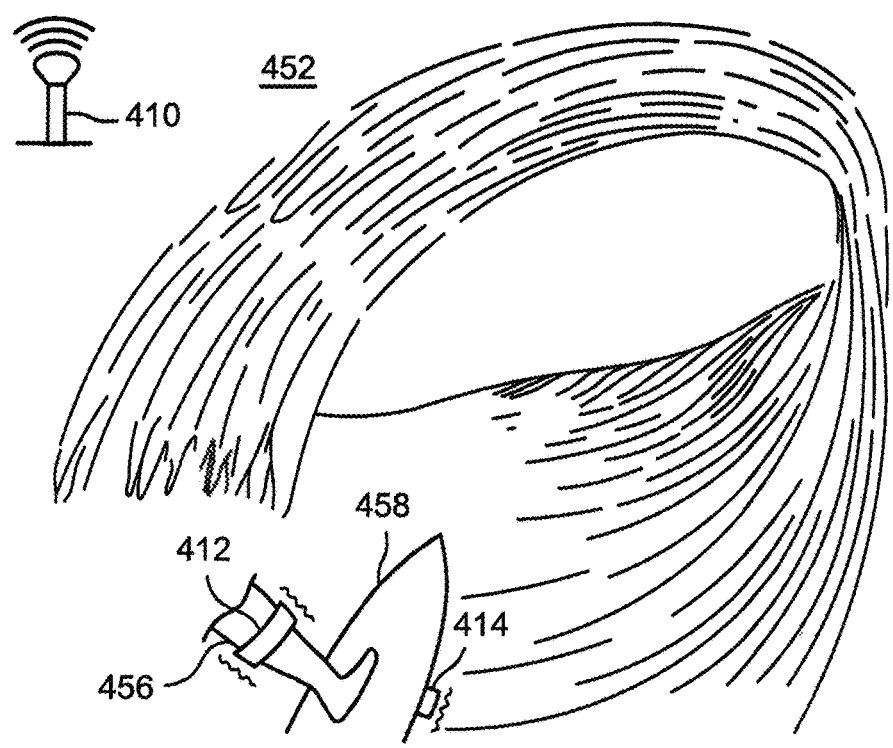

FIG. 4E depicts the surf wave 452, and a vibration device 412 worn by the surfer 456, or a vibration device 414 attached to the surfboard 458, which comprises the sensory cue generator. Upon receiving a sensory cue signal from the sensory cue controller 320, one or both of the vibration devices 412, 414 vibrate with an intensity that is perceptible for the surfer 456, thereby communicating a touch-based sensory cue to the surfer 456. The vibration may be generated in varying intensity, sequence and patterns to communicate different sensory cues to the surfer 456.

Figure 4F:
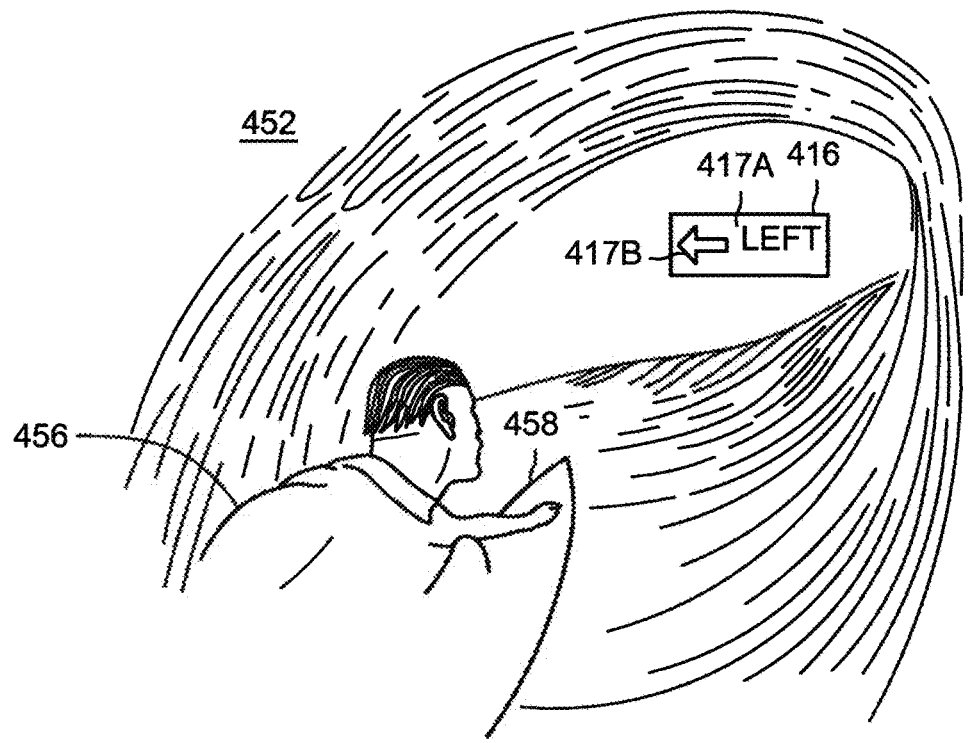

FIG. 4F depicts the surf wave 452, and a digital display 416 visible to the surfer 456 while surfing the surf wave 452, where the digital display 416 comprises the sensory cue generator. Upon receiving a sensory cue signal from the sensory cue controller 320, the digital display 416 displays graphical information, for example an icon 417A or text 417B, which is visible to the surfer, thereby communicating a visual (graphical and textual) sensory cue to the surfer 456. The graphics and text may include arrows or direction text, for example, "LEFT", or a combination of a left arrow icon and the text "LEFT" to indicate to the surfer 456 to maneuver to the left.

Figure 4G:
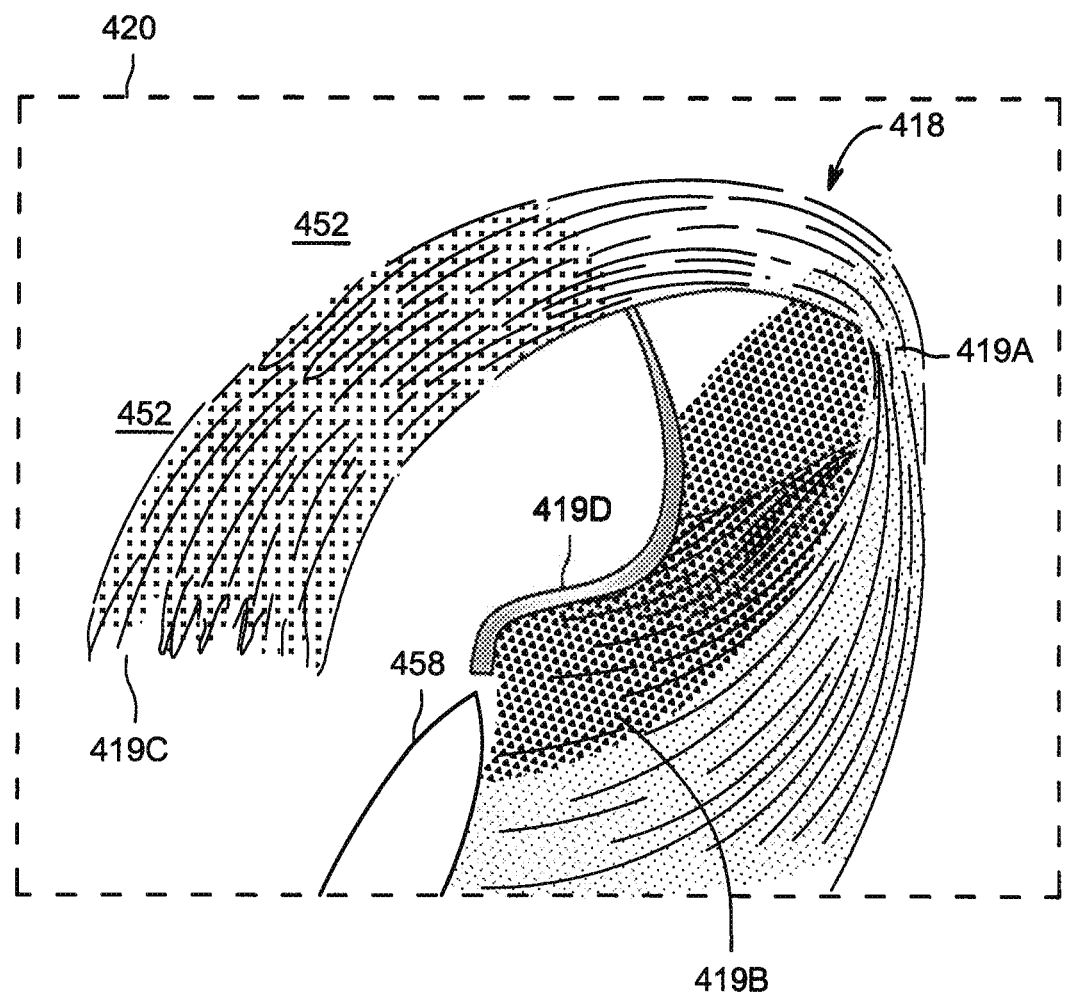

FIG. 4G depicts an augmented reality digital display 420, in which a recommended surfing path 419D, along with other surfing information captured by patterns 419A, 419B, and 419C, overlaid on the surfer's viewpoint while the surfer 456 is surfing the surf wave 452, where the overlaid path 419D and the patterns 419A, 419B, 419C comprise the sensory cue. The augmented reality display 420 is provided by several known devices, for example, GOOGLE GLASS, among several others. Upon receiving a sensory cue signal from the sensory cue controller 320, the augmented reality display 420 overlays one or more of the patterns 419A, 419B, 419C, or 419D one the surfer's viewpoint, thereby communicating a visual sensory cue for maneuvering along the indicated path 419D. Patterns 419A, 419B, 419C may indicate regions to which the surfer 456 should not maneuver, or indicate the conditions of the surf wave, for example, the velocity of the water, turbulence or any other factors affecting surfing conditions in the surf wave 452.

Similar to the embodiment of FIG. 4G, a virtual reality digital display or a digital display such as a television is utilized for visualizing a previously surfed surfing session by the surfer 456 when the surfer 456 is not surfing. For example, the sensory cue controller 320 overlays the surfer's 456 actual path taken during a surfing session of surfing the surf wave 452 over a video of the surfing session, for example a video captured by the camera 348 of FIG. 3B. Such a visualization allows the surfer or a surfing expert to analyze the surfer's 456 maneuvering during the surfing session. In some embodiments, the sensory cue controller 320 further overlays the information regarding the positioning and/or orientation of the surfer's 456 body captured using sensors 349 of FIG. 3B. In some embodiments, the sensory cue controller 320 further overlays a surf path of one or more experts, and/or the body positioning and/or orientation of one or more experts alongside the surfer's 456 surf path and/or the body positioning and/or orientation of the surfer 456, to allow the surfer 456 to compare his or her surfing form with the one or more experts.

A beginning surfer may initially need a comprehensive and extensive sensory cues in order to learn surfing maneuvers. As the surfer gets more experienced with surfing, the extent of sensory cues provided to the surfer may be reduced, depending on the performance of the surfer. In some embodiments, with improved performance or learning of the surfer, the sensory cues provided to the surfer may be further reduced, and in some cases turned off completely. In some embodiments, the sensory cues may be turned off for a period of time, and then turned back on, for example, presented only in certain instances which require complex surfing maneuvers. In some embodiments, the intensity or the perception intensity (for example, light intensity, sound volume, vibration intensity) is decreased, or reduced to zero. Several other patterns of reducing the extent of comprehensiveness of sensory cues would occur to those skilled in the art. In this manner, sensory cues that represent 'training wheels' for a beginning surfer are removed in a gradual manner, as the surfer develops surfing competency.

The techniques and elements described with respect to one embodiment may be combined with the techniques and elements of other embodiments, and all such combinations will occur readily to those skilled in the art without departing from the scope or the spirit of the present invention, as defined by the claims. Further, several techniques discussed herein may be applied to generating sensory cues while a surfer is surfing natural surf waves, for example, via a sensory generator including a virtual or augmented reality display.

According to various embodiments described herein, sensory cue generation as illustrated in FIGS. 2A-2C is implemented without a server, using a sensory cue generator synchronized with the surf wave or the wave generating foil, and sensory cue generation as illustrated in FIGS. 4A-4G is implemented using computing device, for example, the server 310, which generates sensory cue signals for the sensory cue generator. In all embodiments, the generation and delivery of sensory cue is instantaneous, that is the sensory cues are available to the surfer dynamically, in real-time as the surfer surfs the surf wave, and as such, performance may only be constrained by limitations of the processing hardware.

The methods described herein may be implemented in software, hardware, or a combination thereof, in different embodiments. In addition, the order of methods may be changed, and various elements may be added, reordered, combined, omitted or otherwise modified. All examples described herein are presented in a non-limiting manner. Various modifications and changes may be made as would be obvious to a person skilled in the art having benefit of this disclosure. Realizations in accordance with embodiments have been described in the context of particular embodiments. These embodiments are meant to be illustrative and not limiting. Many variations, modifications, additions, and improvements are possible. Accordingly, plural instances may be provided for components described herein as a single instance. Boundaries between various components, operations and data stores are somewhat arbitrary, and particular operations are illustrated in the context of specific illustrative configurations. Other allocations of functionality are envisioned and may fall within the scope of claims that follow. Finally, structures and functionality presented as discrete components in the example configurations may be implemented as a combined structure or component. These and other variations, modifications, additions, and improvements may fall within the scope of embodiments as defined in the claims that follow.

While the foregoing is directed to embodiments of the present invention, other and further embodiments of the invention may be devised without departing from the basic scope thereof, and the scope thereof is determined by the claims that follow.

What is claimed is:

1. A method for providing training to a surfer, comprising:
    delivering a sensory cue to a surfable region on an artificially generated surf wave in motion, the sensory cue for indicating a recommended surfing maneuver to a surfer for surfing the artificially generated surf wave, while the surfer is surfing the artificially generated surf wave,
    wherein the recommended surfing maneuver comprises maneuvering at least one of the surfer's body, or a surfboard used by the surfer, and
    wherein the recommended surfing maneuver is configured to train the surfer while the surfer is surfing in the surfable region.

2. The method of claim 1, wherein the sensory cue is delivered based on at least one of visual recognition of the artificially generated surf wave, or a time synchronization with a wave generation mechanism used to generate the artificially generated surf wave.

3. The method of claim 2, wherein a current position of the artificially generated surf wave is determined based on at least one of visual recognition of the artificially generated surf wave, or a time synchronization with a wave generation mechanism used to generate the artificially generated surf wave.

4. The method of claim 2, wherein the surfable region comprises regions of the surf wave in which the water swells, rises and part of the region in which the water plunges forward to fall creating a barrel or a tube on the surf wave, wherein a current position of the surfer and a current position of the surfboard is determined using at least one of a global positioning system (GPS), cellular communication, Bluetooth, WiFi, a gyroscope, an accelerometer, or a magnetometer.

5. The method of claim 2, wherein the sensory cue includes a light pattern generated by at least one of a first light source positioned outside water in which the artificially generated surf wave is generated or a second light source positioned inside water in which the artificially generated surf wave is generated, a sound, a touch-based sense, or an image or text displayed on a digital display.

6. The method of claim 1, wherein the sensory cue is light generated by a light source mechanically coupled to a wave generation mechanism and positioned to be visible from the surfable region.

* * * * *